United States Patent [19]
Evenden et al.

[11] Patent Number: 5,616,610
[45] Date of Patent: Apr. 1, 1997

[54] (R)-5-CARBAMOYL-8-FLUORO-3-N,N-DISUBSTITUTED-AMINO-3,4-DIHYDRO-2H-1-BENZOPYRANS

[75] Inventors: John L. Evenden, Stockholm; Eva M. Hammarberg, Södertälje; Hans S. Hansson, Stockholm; Sven E. Hellberg; Lars G. Johansson, both of Södertälje; Johan R. M. Lundkvist, Lund; Svante B. Ross; Daniel D. Sohn, both of Södertälje; Seth O. Thorberg, Järna, all of Sweden

[73] Assignee: Astra Aktiebolag, Sodertalje, Sweden

[21] Appl. No.: 362,544

[22] PCT Filed: Oct. 26, 1994

[86] PCT No.: PCT/SE94/01010

§ 371 Date: Jan. 4, 1995

§ 102(e) Date: Jan. 4, 1995

[87] PCT Pub. No.: WO95/11891

PCT Pub. Date: May 4, 1995

Related U.S. Application Data

[63] Continuation-in-part of Ser. No. 144,671, Oct. 28, 1993, Pat. No. 5,420,151, which is a continuation-in-part of Ser. No. 957,214, Oct. 6, 1992, abandoned, and Ser. No. 780,531, Oct. 18, 1991, abandoned, which is a continuation-in-part of Ser. No. 633,247, Dec. 21, 1990, abandoned.

[30] Foreign Application Priority Data

| Dec. 22, 1989 | [SE] | Sweden | 8904361 |
|---|---|---|---|
| Oct. 8, 1991 | [SE] | Sweden | 9102905 |
| Jun. 29, 1992 | [SE] | Sweden | 9202000 |

[51] Int. Cl.⁶ ............... A61K 31/35; C07D 311/20
[52] U.S. Cl. ............................... 514/456; 549/404
[58] Field of Search ........................... 549/404; 514/456

[56] References Cited

U.S. PATENT DOCUMENTS

| 4,683,223 | 7/1987 | Trivedi | 514/46 |
|---|---|---|---|
| 4,801,605 | 1/1989 | Hutchinson | 514/432 |
| 4,873,262 | 10/1989 | Junge et al. | 514/510 |
| 4,971,982 | 11/1990 | Attwood et al. | 549/404 |
| 5,026,707 | 6/1991 | Nixon | 514/255 |
| 5,082,858 | 1/1992 | Garcia et al. | 514/456 |
| 5,143,936 | 9/1992 | Yamanaka et al. | 514/456 |
| 5,214,156 | 5/1993 | Andersson et al. | 549/75 |
| 5,225,596 | 7/1993 | Carlsson et al. | 564/426 |
| 5,286,753 | 2/1994 | Schaus et al. | 514/657 |
| 5,306,830 | 4/1994 | Andersson et al. | 549/404 |
| 5,420,151 | 5/1995 | Hammarberg | 514/465 |

FOREIGN PATENT DOCUMENTS

| 0222996 | 5/1987 | European Pat. Off. |
|---|---|---|
| 0231139 | 8/1987 | European Pat. Off. |
| 0280269 | 8/1988 | European Pat. Off. |
| 0343830 | 11/1989 | European Pat. Off. |
| 0385658 | 9/1990 | European Pat. Off. |
| 8804654 | 6/1988 | WIPO. |
| 9109983 | 7/1991 | WIPO. |

OTHER PUBLICATIONS

Kennett, et al. "Antidepressant-like action of 5-HT$_{1A}$ Agonists and conventional antidepressants in an animal model of depression", Eur. J. Pharm. 134:265–274, 1982.
Lockhart, et al., Journal of Medicinal Chemistry, vol. 15, No. 8, pp. 863–865 (1972).
Archer, et al. "(+)-8-OH-DPAT and MeODMT Induced Analgesia is Antagonised by Noradrenaline Depletion", Physiol. and Beh. 39:95–102, 1987.
Hjorth, S. "Hypothermia in the Rat Induced by the Potent Serotoninergic Agent 8-OH-DPAT", J. Neur. Transm. pp. 131–135, 1985.
Bowen, et al. "Circumscribed changes of the cerebral cortex in neuropsychiatric disorders of later life", Proc. Natl. Acad. Sci. (USA) 86:9504–9508, 1989.
Dabire, et al. "Comparison of effects of some 5-HT$_1$ agonists on blood pressure and heart rate of normotensive anaesthesized rats", Eur. J. Pharm. 140:259–266, 1987.
Traber, et al. "5-HT$_{1A}$ receptor-related anxiolytics", TIPS, 8:432–437, 1987.
Samanin, et al. "Serotonin and the Pharmacology of Eating", Annals N.Y. Acad. Sci. 575:194–208, 1989.
SCRIP's Serotonin Report No. 1184, 1987.
Hutchinson et al. "Preparation of 3-Aminodihydro [1]benzopyran and Benzothiopyran Derivatives as Seratoninergic Agonists", Chem. Abs. 107:39617j. (1987).
Hershenson, et al. "Annual Reports in medicinal, Chemistry", D. Bailey Ed., 21:31–40, Acad. Press, N.Y., 1986.
Foye, W. "Principles of Medicinal Chemistry", 2nd ed. pp. 80–81, Lea & FEbiger, Philadelphia, 1981.

*Primary Examiner*—S. Mark Clardy
*Assistant Examiner*—Mary C. Cebulak
*Attorney, Agent, or Firm*—White & Case

[57] ABSTRACT

Compounds of the general formula

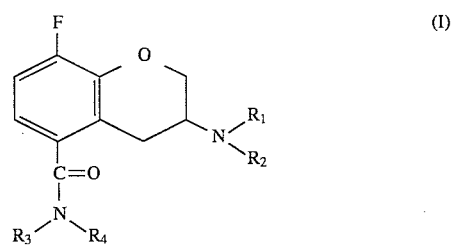

(I)

wherein $R_1$ is n-propyl or cyclobutyl;

$R_2$ is isopropyl, tertiary butyl, cyclobutyl, cyclopentyl or cyclohexyl;

$R_3$ is hydrogen;

$R_4$ is hydrogen or methyl;

as (R)-enantiomer in the form of free base or pharmaceutically acceptable salts thereof, process for their preparation, pharmaceutical composition, use of and method of treatment of disorders in CNS.

16 Claims, No Drawings

(R)-5-CARBAMOYL-8-FLUORO-3-N,N-DISUBSTITUTED-AMINO-3,4-DIHYDRO-2H-1-BENZOPYRANS

This application is a continuation-in-part of application Ser. No. 08/144,671, filed Oct. 28, 1993 (now U.S. Pat. No. 5,420,151), which is a continuation-in-part of application Ser. No. 07/957,214, filed Oct. 6, 1992 (abandoned) and Ser. No. 07/780,531, filed Oct. 18, 1991 (abandoned), which in turn is a continuation-in-part of application Ser. No. 07/633,247, filed Dec. 21, 1990 (abandoned).

This application is a 371 of PCT/SE94/01010 filed Oct. 26, 1994.

FIELD OF THE INVENTION

The present invention relates to the new compounds, (R)-5-carbamoyl-8-fluoro-3-N,N-disubstituted-amino-3,4-dihydro-2H-1-benzopyrans in the form of free base or pharmaceutically acceptable salts thereof, process for their preparation, pharmaceutical compositions containing said therapeutically active compounds and to the use of said active compounds in therapy.

An object of the invention is to provide compounds for therapeutic use, especially compounds having a highly selective affinity for a subgroup of 5-hydroxytryptamine receptors, namely the $5HT_{1A}$-receptor in the central nervous system (CNS) of mammals including man and which compounds at the same time shows antagonist activity.

It is also an object of the invention to provide compounds with a therapeutic effect after oral administration.

PRIOR ART

Halogenated-5-subst/unsubst carbamoyl-3-(N,N-disubstituted-amino)-3,4-dihydro-2H-1-benzopyrans intended for therapeutic use in the central nervous system, especially having $5-HT_{1A}$ receptor affinity, are already disclosed in the international patent application WO 91/09853.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occuring in depressed patients. The invention concerns compounds which have an effect on 5-HT neurotransmission.

Serotonin, or 5-HT, activity is thought to be involved in many different types of psychiatric disorders. For instance it is thought that an increase in 5-HT activity is associated with anxiety, while a decrease in 5-HT release has been associated with depression. Serotonin has in addition been implicated in such diverse conditions as eating disorders, gastrointestinal disorders, cardiovascular regulation and sexual behavior.

The 5-HT Receptors

The various effects of serotonin may be related to the fact that serotonergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as $5-HT_1$, $5-HT_2$, $5-HT_3$, $5-HT_4$, $5-ht_5$, $5-ht_6$ and $5-ht_7$ with the $5-HT_1$ receptor further divided into the $5-HT_{1A}$, $5-HT_{1B}$, $5-HT_{1D}$, $5-HT_{1E}$ and $5-HT_{1F}$ subtypes. Each receptor subtype is involved in a different serotonin function and has different properties.

The $5-HT_{1A}$-subtype Receptors

With respect to the 5-HT1A subtype receptors, these receptors have also been further differentiated depending on their neuronal location thereby resulting in different modes of action and physiological functions. For example, the $5-HT_{1A}$ inhibitory autoreceptor is located presynaptically on cellbodies of 5-HT neurons. When 5-HT or a $5-HT_{1A}$ agonist activates such an inhibitory autoreceptor, the firing rate of the 5-HT neuron is depressed. Since the neuron does not fire, the release of 5-HT into the synapse is also decreased. In this case, a $5-HT_{1A}$ agonist acts as an artificial transmitter substance mimicking the effect of 5-HT with the result of decreasing the release of 5-HT from the central nervous system neurons. The $5-HT_{1A}$ agonist on the inhibitory autoreceptor thus acts as an anxiolytic or antianxiety drug.

The use of a 5-HT blocking agent at the autoreceptor will thus allow the neuron to increase its firing resulting in an increased release of 5-HT at the terminal synapses. A $5-HT_{1A}$ antagonist would thus improve the 5-HT neurotransmission and produce an antidepressant effect making it useful as a medication for depression.

Other localizations of $5-HT_{1A}$ subtype receptors also exist. These postsynaptic $5-HT_{1A}$ receptors are located downstream on other neurons in the synaptic region. In contrast to the inhibitory autoreceptors, activation of the postsynaptic $5-HT_{1A}$ receptors results in stimulation of a very characteristic behavioral syndrome in animals, the 5-HT syndrome. The agonist, partial agonist, antagonist profile of an agent on the $5-HT_{1A}$ postsynaptic receptor cannot be predicted from its activity profile on the $5-HT_{1A}$ inhibitory autoreceptor. Thus, any given $5-HT_{1A}$-selective compound may show different activity profiles on each of these receptors. For example, the $D_2$ antagonist Buspirone also functions as an agonist on the $5-HT_{1A}$ autoreceptor and acts as a weak partial agonist or antagonist on the $5-HT_{1A}$ postsynaptic receptor. Other compounds such as the substituted aminotetralin 8-hydroxy-2-(dipropylamino)-tetralin ("8-OH-DPAT"), which is considered the standard for $5-HT_{1A}$ agonist activity, is a full agonist on both the inhibitory autoreceptor and on the postsynaptic receptor.

The receptor activity profile, even within a specific sub-receptor group such as $5-HT_{1A}$ is therefore unpredictable and may therefore result in different pharmacological profiles.

The object of the present invention is to provide compounds for therapeutic use, especially for treatment of 5-hydroxytryptamine mediated disorders in the central nervous system for instance depression, anxiety, obsessive-compulsive disorder (OCD), anorexia, bulimia, senile dementia, migraine, stroke, Alzheimer's disease, cognitive disorders, hypertension, gastrointestinal disorders, thermoregulatory and sexual disturbances, pain and for treatment of disturbances in the cardiovascular system.

DISCLOSURE OF THE INVENTION

The object of the present invention is to provide compounds having a selective $5-HT_{1A}$ receptor affinity and at the same time being an antagonist, as well as having a good bioavailability.

Surprisingly, it has been found that the (R)-enantiomer of the compounds of the formula I

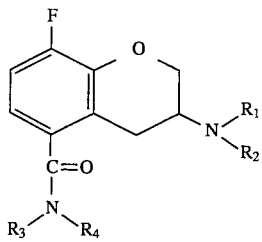

wherein
$R_1$ is n-propyl or cyclobutyl;
$R_2$ is isopropyl, tertiary butyl, cyclobutyl, cyclopentyl or cyclohexyl;
$R_3$ is hydrogen;
$R_4$ is hydrogen or methyl;
in the form of free base or pharmaceutically acceptable salts thereof, possess a high affinity to the specific subgroup of $5-HT_{1A}$ receptor in CNS and act as antagonists on that $5-HT_{1A}$ receptor, and as well show sufficient bioavailability after oral administration.

Compounds of the present invention are those having the nitrogen atom on the carbamoyl group unsubstituted or mono substituted with a methyl group. The 8-fluoro substituent in combination with unsubstitution or substitution with a small group as $CH_3$ on the carbamoyl group is very important when going from partial agonist to antagonist activity.

Further, the compounds of the present invention are those having at least one branched or cyclic alkyl group having 3 to 6 carbon atoms in the carbon group on the 3-amino group, thus only one of the substituents may be a normal propyl group. The branching or cyclisation of the alkyl group on the amino group seem to be essential to obtain a sufficient bioavailability.

Furthermore, it has been found that a high affinity for the $5-HT_{1A}$ receptor in CNS in combination with antagonist activity is strictly stereospecific to the (R)-enantiomer of the compounds of the invention.

Examples of compounds of the present invention are:
(R)-3-(N-Cyclopentyl-N-n-propylamino)-8-fluoro-5-methylcarbamoyl-3,4-dihydro-2H-1-benzopyran
(R)-8-Fluoro-3-(N-isopropyl-N-n-propylamino)-5-carbamoyl-3,4-dihydro-2H-1-benzopyran
(R)-5-Carbamoyl-3-(N-tert-Butyl-N-n-propylamino)-8-fluoro-3,4-dihydro-2H-1-benzopyran
(R)-5-Carbamoyl-3-(N,N-dicyclobutylamino)-8-fluoro-3,4-dihydro-2H-1-benzopyran
(R)-5-Carbamoyl-3-(N-cyclobutyl-N-propylamino)-8-fluoro-3,4-dihydro-2H-1-benzopyran
(R)-5-Carbamoyl-3-(N-cyclobutyl-N-isopropylamino)-8-fluoro-3,4-dihydro-2H-1-benzopyran
(R)-5-Carbamoyl-3-(N-cyclopentyl-N-n-propylamino)-8fluoro-3,4-dihydro-2H-1-benzopyran
(R)-5-Carbamoyl-3-(N-cyclohexyl-N-n-propylamino)-8fluoro-3,4-dihydro-2H-1-benzopyran
(R)-5-Carbamoyl-3-(N-cyclopentyl-N-cyclobutylamino)-8-fluoro-3,4-dihydro-2H-1-benzopyran The compounds of the present invention are in the form of the (R)-enantiomer and in the form of free base or pharmaceutically acceptable salt thereof. Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, pamoic, ethanedisulfonic, sulfamic, succinic, propionic, glycollic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphtoic, nicotinic, methanesulfonic, ethanesulfonic, hydroxyethanesulfonic, benzenesulfonic, p-toluenesulfonic, sulfanilic, naphthalenesulfonic, ascorbinic, cyclohexylsulfamic, fumaric, maleic and benzoic acids. These salts are readily prepared by methods known in the art.

METHODS OF PREPARATION

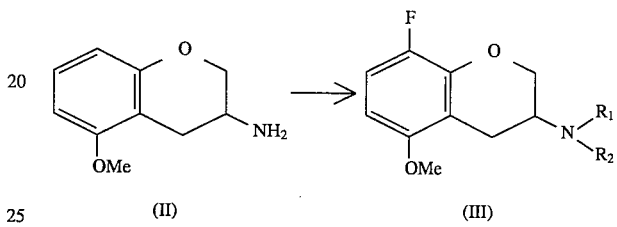

The preparation of (R)-3-amino-5-methoxy-3,4-dihydro-2H-1-benzopyran (compound II) is described in WO93/07135. The preferred method for the introduction of fluorine is by brominating the aromatic ring, selectively, in the 8-position. Bromination can be done by using bromine with or without a catalyst. Other brominating agents can be used e.g. HOBr and N-bromo amides (especially N-bromosuccinimide). Suitable solvents for bromination are acetic acid, dioxane and chlorinated solvents e.g. methylene chloride.

Before fluorination the primary amine must be fully alkylated by $R_1$ and by $R_2$ as stated above or protected by a suitable group that can be removed later e.g. dibenzyl. Introduction of the alkyl groups on nitrogen can be done by reductive amination from the appropriate aldehyde or ketone using a suitable reducing agent e.g. $NaCNBH_3$ or catalytically with $H_2$ and a suitable catalyst containing palladium, platina or nickel in a suitable solvent e.g. tetrahydrofuran (THF), dioxane, methanol or ethanol. Introduction of the alkyl groups can also be done by alkylation with the appropriate alkyl halide e.g. Cl, Br or I, or by an activated alcohol e.g. alkyl-mesylate or -tosylate in a suitable solvent e.g. dimethylformamide (DMF), acetone or acetonitrile with a suitable base e.g. $K_2CO_3$. Fluorination can then occur by lithiation of the bromo compound with an alkyllithium reagent e.g. n-butyllithium and followed by the reaction with a suitable fluorinating agent preferably a N-fluoro-N-alkyl-/arylsulfonamide e.g. N-fluorobenzenesulfonimide. The solvent for this reaction can be anhydrous alkyl ethers e.g. tetrahydrofuran (THF) or diethyl ether, or non-protic solvents e.g. hexane or benzene. The temperature range can vary from $-100°$ C. to room temperature but preferably $-78°$ C. to $-20°$ C.

The compounds of the invention may be prepared from the compound (R)-3-amino-8-fluoro-5-methoxy-3,4-dihydro-2H-1-benzopyran (as described above) followed by known methods such as reductive amination, N-alkylation, demethylation and conversion to the leaving group Y to obtain compound IV.

The compound of formula I of the invention may be prepared according to the following methods:

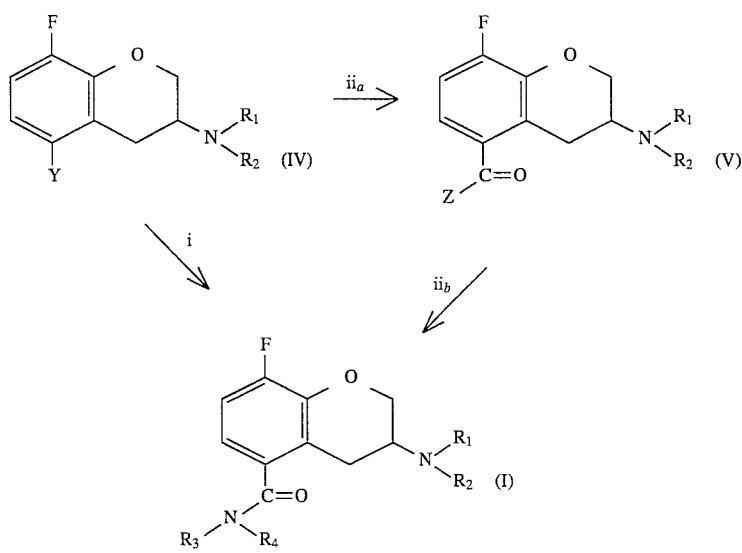

i, converting directly the compounds of formula IV

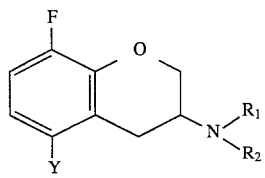

wherein Y is a leaving group such as trifluoromethane sulfonate ($OSO_2CF_3$), halide e.g. Cl, Br or I by a catalytic cycle using a zerovalent transition metal (M) such as Pd or Ni, which may be generated in situ and undergoes an oxidative addition to the aryl-Y-bond. Treatment with carbon monoxide followed by amination with the proper amine (ammonia or methylamine) give the compounds of formula I, whereafter if desired it is converted to a salt. ii, Alternatively, the compounds of formula IV is converted to the compounds of formula V

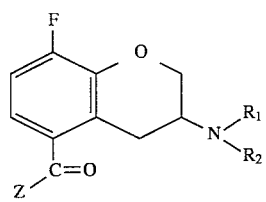

wherein Z is Cl, Br, OH or $OR_p$, where $R_p$ is $C_1$–$C_6$ alkyl, by a catalytic cycle using a zerovalent transition metal, with ability to undergo oxidative addition to aryl-Y-bonds e.g. the aryl-$OSO_2CF_3$ bonds. The aryl-CO-metal-Y complex is formed by treatment with carbon monoxide (CO).

Further reagents are an alcohol such as methanol, ethanol, a tertiary amine such as a trialkylamine e.g. triethylamine in an inert organic solvent preferentially a polar aprotic solvent such as dimethylformamide (DMF), dimethylsulfoxide (DMSO), dioxane, tetrahydrofuran (THF), acetone, acetonitrile etc. The reaction is normally performed at a temperature between +40° to +120° C. and at a pressure between 100 to 500 kPa (ii). This is optionally followed by hydrolysis and treatment with a thionyl halide e.g. thionyl chloride, to obtain the corresponding acid halide derivative.

The compounds of formula V is aminated ($ii_b$) with the proper amine (ammonia or methylamine) in a solvent e.g. toluene, methylene chloride, benzene, water at reflux temperature or between 0°–100° C. to give the compounds of formula I.

Pharmaceutical Preparations

According to the present invention the compound of the invention will normally be administered orally, rectally or by injection, in the form of pharmaceutical preparations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft, gelatine capsules, the active substance may be admixed with e.g. a vegetable oil or poly-ethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethyl-cellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules. Suitable daily doses of the compound of the invention in therapeutic treatment of humans are about 0.01–100 mg/kg bodyweight at peroral administration and 0.001– 100 mg/kg bodyweight at parenteral administration.

The invention is illustrated by the following working examples.

PREPARATION OF STARTING MATERIALS

Preparation 1

(R)-3-Amino-8-fluoro-5-methoxy-3,4-dihydro-2H-1-benzopyran a) (R) -3-Amino-8-bromo-5-methoxy-3,4-dihydro-2H-1-benzopyran (R)-3-Amino-5-methoxy-3,4-dihydro-2H-1-benzopyran (25 g, 0.14 mol) and anhydrous sodium acetate (34 g, 0.42 mol) were dissolved in acetic acid (500 mL). Bromine (23.4 g, 0.15 mol), dissolved in acetic acid (500 mL), was added dropwise at room temperature. The addition of bromine continued for about 7 days. The solvent was removed in vacuo and the residue was dissolved in sodium hydroxide (25%)/diethyl ether (exothermic reaction, the mixture was cooled in an ice-bath). The layers were separated and the alkaline water-phase was extracted thrice with diethyl ether. The combined ether layers were dried ($Na_2SO_4$) and the solvent was removed in vacuo to give 35.5 g of an oily residue. The oil was dissolved in diethyl ether and the solution was cooled with an ice-bath (0° C.). HCl, dissolved in diethyl ether, was added dropwise until the suspension became acidic (controlled with pH paper). The crystals were filtered and then recrystallized from methanol to give the title compound in 70% yield (28.5 g). Mp: 281°–282°C. The HCl salt was partitioned between diethyl ether and 2M $NH_3$ (aq) and the free base was obtained by extraxtions of the alkaline water phase with diethyl ether. $[\alpha]^{21}_D$=+40° (C=0.1, HCl salt in MeOH). GC-MS (70 eV) M+1=259 (53%).

b) (R) -8-Bromo-3-(N,N-dibenzylamino)-5-methoxy-3,4-dihydro-2H-1-benzopyran (R)-3-Amino-8-bromo-5-methoxy-3,4-dihydro-2H-1-benzopyran (11.5 g, 44 mmol) was dissolved in 400 mL anhydrousacetonitrile and to the reaction were benzyl bromide (13 mL, 110 mmol), anhydrous potassium carbonate (grounded) (16 g, 116 mmol), and a catalytic amount of KI added and then heated to 85° C. for 48 h. The solvent was removed in vacuo, the remains were taken into a 2M solution of $NH_3$ and then extracted twice with ether. The combined ether portions were treated with brine, dried ($MgSO_4$), filtered, and the solvent removed in vacuo to give the crude residue. Chromatography on silica (eluent: $CH_2Cl_2$) gave 15 g (78% yield) of the title compound as a clear oil. $[\alpha]^{21}_D$=–15.5° (C=0.1 CHCl3) GC-MS (70eV) M=437 (15%).

c) (R)-3-(N,N-Dibenzylamino)-8-fluoro-5-methoxy-3,4-dihydro-2H-1-benzopyran (R)-8-Bromo-3-(N,N-dibenzylamino)-5-methoxy-3,4-dihydro-2H-1-benzopyran (4.35 g, 9.9 mmol) was dissolved in 45 mL of anhydrous THF and cooled to –78° C. To this was a 1.6M n-BuLi solution (6.8 mL, 10.9 mmol) added dropwise and allowed to stir at –78° C. for 1 h. N-Fluorobenzenesulfonimide (3.8 g, 11.9 mmol), dissolved in 30 mL anhydrous THF, was added dropwise under 45 min and allowed to stir at –78° C. for 1 h. The reaction was stopped by adding 3 mL saturated $NH_4Cl$ followed by 9 mL of a solution comprised of 2 g of $NH_2OHxHCl$ and 8 g of $Na_2CO_3$ in 100 mL of $H_2O$ and allowing the reaction to warm to room temperature. A 2M $NH_3$ solution was added and the reaction was extracted twice with ether, treated with brine, dried ($Na_2SO_4$), filtered, and evaporated in vacuo to give the crude product.

Purification of the 8-fluoro (desired) from the 8-hydrogen (15%) compound was carried out by a crude chromatography (eluent: 25% $CH_2Cl_2$/hexane) to give 1.78 g. The crude was rechromatographed on silica (eluent: 3% acetone/hexane) to give 1.50 g (40% yield) of the title compound as a clear oil $[\alpha]^{21}_D$=–112.1° (C=0.1, CHCl3). GC-MS (70 eV) M=377 (37%).

d) (R)-3-Amino-8-fluoro-5-methoxy-3,4-dihydro-2H-1-benzopyran (R)-3-(N,N-Dibenzylamino)-8-fluoro-5-methoxy-3,4-dihydro-2H-1-benzopyran (13.0 g, 34.4 mmol) was dissolved in 265 mL methanol and 115 mL THF. To this was 10% Pd/C (4 g) and ammonium formate (51.5 g, 0.817 mol) added. The reaction was heated to 50° C. for 2.5 h. The reaction was filtered and the solvent was removed in vacuo, the remains were taken into a 2 M solution of NaOH and then extracted twice with ether. The combined ether portions were treated with brine, dried ($Na_2SO_4$), filtered, and the solvent removed in vacuo to give 6.2 g (91% yield) of the title compound as a clear oil. $[\alpha]^{21}_D$=–15.3° (C=1 $CHCl_3$) GC-MS (70 eV) M=197 (51%).

Preparation 2

(R)-8-Fluoro-3-(N-isopropyl-N-propylamino)-5-trifluoromethylsulfonyloxy-3,4-dihydro-2H-1-benzopyran a) (R)-8-Bromo-3-(N-isopropylamino)-5-methoxy-3,4-dihydro-2H -1-benzopyran (R)-3-(N-Isopropylamino)-5-methoxy-3,4-dihydro-2H-1-benzopyran (4.02 g, 18.2 mmol) and anhydrous sodium acetate were dissolved in acetic acid (80 mL). To the stirred mixture was bromine (0.93 mL, 18.2 mmol) dissolved in acetic acid (40 mL) added dropwise under 1.5 h. The solvent was removed in vacuo, taken into a 2M NaOH solution and extracted twice with diethyl ether. The combined ether portions were treated with brine, dried ($Na_2SO_4$), filtered, and the solvent was removed in vacuo to give the crude residue. The hydrochloride salt was made by dissolving the pure base in diethyl ether and adding an excess of an ethereal HCl solution to give a white solid. The salt was recrystallized twice from ethanol/diethyl ether to give 3.8 g (62% yield) Mp: 257°–8° C. $[\alpha]^{21}{}_D=-97.7°$ (C=0.1 $CHCl_3$). The free base was made from the hydrochloride salt to give an oil. GC-MS (70 eV) M=301 (100%).

b) (R)-8-Bromo-3-(N-isopropyl-N-propylamino)-5-methoxy-3,4-dihydro-2H-1-benzopyran (R)-8-Bromo-3-(N-isopropylamino)-5-methoxy-3,4-dihydro-2H-1-benzopyran (3.8 g, 11.3 mmol) was dissolved in anhydrous methanol (80 mL) and to this was propanal (8.1 mL, 0.113 mol) added. The reaction was cooled (ice-bath) then sodium cyanoborohydride (1.3 g, 20.3 mmol) was added, the pH was adjusted to 5, and the reaction was allowed to stir at room temperature overnight. The solvent was removed in vacuo, the remains were twice with diethyl ether. The combined ether portions were treated with brine, dried ($Na_2SO_4$) filtered, and taken into a 1M solution of $Na_2CO_3$ and then extracted the solvent removed in vacuo to give the crude residue. Chromatography on silica (eluent: 7% ethyl acetate/hexane) gave 3.75 g (97% yield) of the title compound as a clear oil $[\alpha]^{21}{}_D=-82.5°$ (C=0.1 CHCl3). GC-MS (70 eV) M=343 (29%). The hydrochloride salt was made by dissolving the base in diethyl ether and dropping an excess of an ethereal HCl solution. The salt was recrystallized from ethanol/diethyl ether to give a white solid. Mp: 177°–9° C.

c) (R)-8-Fluoro-3-(N-isopropyl-N-propylamino)-5-methoxy-3,4-dihydro-2H-1-benzopyran (R)-8-Bromo-3-(N-isopropyl-N-propylamino)-5-methoxy-3,4-dihydro-2H-1-benzopyran (2.3 g, 6.72 mmol) was dissolved in anhydrous THF (25 mL) and cooled to −78° C. To this was a 1.6M n-BuLi solution (4.83 mL, 7.73 mmol) added dropwise and allowed to stir at −78° C. for 1 h. N-Fluorobenzenesulfonimide (2.55 g, 8.06 mmol), dissolved in anhydrous THF (15 mL), was added dropwise under 20–30 min and allowed to stir at −78° C. for 4 h. The reaction was stopped by adding 1 mL of a saturated aqueous $NH_4Cl$ solution followed by 3 mL of a solution comprised of 2 g of $NH_2OHxHCl$ and 8 g of $Na_2CO_3$ in 100 mL of $H_2O$ and allowing the reaction to warm to room temperature. A 2M $NH_3$ solution was added and the reaction was extracted, twice, with diethyl ether, treated with brine, dried ($Na_2SO_4$), filtered, and evaporated in vacuo to give the crude product. Chromatography on silica (eluent: chloroform) gave 1.0 g (53% yield) of the title compound as a clear oil. $[\alpha]^{21}{}_D=-89.2°$ (C=0.1 $CHCl_3$) GC-MS (70 eV) M=281 (32%).

The hydrochloride salt was made by dissolving the pure base in diethyl ether and dropping an excess of an ethereal HCl solution to give a white solid (sinters at 80° C).

d) (R)-8-Fluoro-3-(N-isopropyl-N-propylamino)-5-hydroxy-3,4-dihydro-2H-1-benzopyran (R)-8-Fluoro-3-(N-isopropyl-N-propylamino)-5-methoxy-3,4-dihydro-2H-1-benzopyran hydrochloride (1.03 g, 3.24 mmol) was dissolved in anhydrous $CH_2Cl_2$ (30 mL) and cooled to −40° C. To the solution was $BBr_3$ (0.77 mL, 8.1 mmol), dissolved in anhydrous $CH_2Cl_2$ (5 mL), added dropwise. The cooling-bath was removed and after 3 h at room temperature the reaction was complete. The reaction was poured out onto an ice/2M $NH_3$ solution and the mixture was extracted, twice, with diethyl ether. The combined ether portions were treated with brine, dried ($Na_2SO_4$), filtered, and the solvent removed in vacuo to give the crude residue. Chromatography on silica (eluent: 20% ethyl acetate/hexane) gave 0.84 g (97% yield) of the title compound as a clear oil $[\alpha]^{21}{}_D=-94.2°$ (C=0.1 CHCl3) GC-MS (70 eV) M=267 (26%). The hydrochloride salt was made by dissolving the pure base in diethyl ether and dropping an excess of an ethereal HCl solution. The salt was recrystallized from $CHCl_3$/diethyl ether/ethyl acetate to give a white solid. Mp: 220°–2° C.

e) (R)-8-Fluoro-3-(N-isopropyl-N-propylamino)-5-trifluoromethylsulfonyloxy-3,4-dihydro-2H-1-benzopyran (R)-8-Fluoro-3-(N-isopropyl-N-propylamino)-5-hydroxy-3,4-dihydro-2H-1-benzopyran (0.71 g, 2.66 mmol) and collidine (0.49 mL, 3.72 mmol) were dissolved in anhydrous $CH_2Cl_2$ (25 mL) and cooled to −40° C. Trifluoromethanesulfonic anhydride (0.54 mL, 3.2 mmol) was added dropwise and allowed to warm to ambient temperature, and after coming to 0° C. the reaction was done. The reaction was diluted with $CH_2Cl_2$ and washed with a saturated aqueous $NaHCO_3$ solution, dried ($MgSO_4$), filtered, and evaporated in vacuo to give a crude residue. Chromatography on silica (eluent: $CH_2Cl_2$) gave 0.82 g (77% yield) of the title compound as a clear oil. $[\alpha]^{21}{}_D=-85.5°$ (C=0.1, CHCl3). GC-MS (70 eV) M=399 (6%).

EXAMPLE 1

1R)-3-(N-Cyclopentyl-N-n-pryopylamino)-8-fluoro-5-N-methylcarbamoyl-3,4-dihydro-2H-1-benzopyran a) (R)-3-N-Cyclopentylamino-8-fluoro-5-methoxy-3,4-dihydro-2H-1-benzopyran (R)-3-Amino-8-fluoro-5-methoxy-3,4-dihydro-2H-1-benzopyran (1.5 g, 7.6 mmol), acetic acid (0.45 g, 7.6 mmol), and cyclopentanone (2.5 g, 3 mmol) were dissolved in 30 ml of methanol. With stirring, sodiumcyanoborohydride (0.8 g, 13 mmol) was added in portions under a few minutes. Stirring was continued for 2 hours. A GC sample showed 100% of a new product. The solvent was evaporated and water, 2M $NH_3$ and EtOAc were added. The organic layer was separated and washed with water. The layer was dried with $Na_2SO_4$ and evaporated to give 1.3 g (64% yield) of a colourless oil. GC/MS with the molecular peak of 265 confirmed the title compound.

b) (R)-3-(N-Cyclopentyl-N-n-propylamino)-8-fluoro-5-methoxy-3,4-dihydro-2H-1-benzopyran (R)-3-N-Cyclopentylamino-8-fluoro-5-methoxy-3,4-dihydro-2H-1-benzopyran (1.3 g, 5 mmol), acetic acid (0.3 g, 5 mmol) and propionaldehyde (1.5 g, 25 mmol) were dissolved in 30 ml of methanol. With stirring, sodiumcyanoborohydride (0.8 g, 13 mmol) was added in portions under a few minutes and stirring was continued. After 3 hours a GC sample showed 100% of a new product. The solvent was evaporated and water, 2 molar $NH_3$ and EtOAc were added. The organic layer was separated and washed neutral with water. The layer was dried with $Na_2SO_4$ and evaporated to give 1 g (65% yield) of a colourless oil. GC/MS with the molecular peak of 307 confirmed the title compound.

c) (R)-3-(N-Cyclopentyl-N-n-propylamino)-8-fluoro-5-hydroxy-3,4-dihydro-2H-1-benzopyran (R)-3-(N-Cyclopentyl-N-n-propylamino)-8-fluoro-5-methoxy-3,4-dihydro-2H-1-benzopyran (1 g, 5 mmol) was dissolved in 25 ml of $CH_2Cl_2$. An excess of etheric HCl was added to form the HCl salt. A solution of $BBr_3$ (4 g, 15 mmol) in 10 ml of $CH_2Cl_2$ was prepared and added dropwise under 10 minutes with stirring (ice-bath). The reaction mixture was allowed to reach room temperature during continued stirring for 6 hours and the mixture was poured out into ice water and made alkaline by adding ammonia. The organic layer was separated, dried with $Na_2SO_4$ and evaporated to afford a dark brown oil. Chromatography ($SiO_2$, di-isopropyl ether and hexane 1+1) afforded 1.1 g of an colourless oil. The HCl salt was prepared from the base and etheric HCl and rerystallized from acetonitrile to give 0.85 g (52% yield). Mp 220°–221°C.

d) (R)-3-(N-Cyclopentyl-N-n-propylamino)-8-fluoro-5-trifluoromethylsulfonyloxy-3,4-dihydro-2H-1-benzopyran (R)-3-(N-Cyclopentyl-N-n-propylamino)-8-fluoro-5-hydroxy-3,4-dihydro-2H-1-benzopyran (0.7 g, 3 mmol) was dissolved in 25 ml of $CH_2Cl_2$ and triethylamine (0.3 g, 3 mmol) was added. The solution of trifluoromethanesulfonic anhydride (1 g, 4 mmol) in 5 ml of $CH_2Cl_2$ was added dropwise under 10 min (–20° C.). Stirring was continued for 1 hour. The reaction mixture was poured out into ice water and the pH was adjusted to 8 by addition of ammonia and extracted by ether. The organic layer was separated, dried with $Na_2SO_4$ and evaporated to afford a brown oil. Chromatography ($SiO_2$, $CH_2Cl_2$+hexane, 1+3) afforded 0.5 g (44% yield) of a colourless oil. GC/MS with the molecular peak of 425 confirmed the title compound.

e) (R)-3-(N-Cyclopentyl-N-n-propylamino)-8-fluoro-5-N-methylcarbamoyl-3,4-dihydro-2H-1-benzopyran (R)-3-(N-Cyclopentyl-N-n-propylamino-8-fluoro-5-trifluoromethylsulfonyloxy-3,4-dihydro-2H-1-benzopyran (0.5 g, 1 mmol) was dissolved in 15 ml of 1,4-dioxane. Palladium II acetate (10 mg), 1,3-bis (diphenylphosphino)-propane (20 mg), and methylamine (0.15 g, 5 mmol) were added and the mixture was stirred in carbon monoxide atmosphere over night at 70° C. Evaporation and chromatography ($SiO_2$, diethyl ether+hexane 1+3) afforded the final compound as a colourless oil. The HCl salt was prepared to give 0.24 g (65% yield) of white crystals. Mp 108° C.

EXAMPLE 2

(R)-8-Fluoro-3-(N-isopropyl-N-n-propylamino)-5-carbamoyl-3,4-dihydro-2H-1-benzopyran a) Methyl (R)-8-fluoro-3-(N-isopropyl-N-n-propylamino)-3,4-dihydro-2H-1-benzopyran-5-carboxylate (R)-8-Fluoro-3-(N-isopropyl-N-n-propylamino)-5-trifluoromethanesulfonyloxy-3,4-dihydro-2H-1-benzopyran (2.4 g, 6.0 mmol), triethylamine (1.3 g, 12.9 mmol), 1,3-bis (diphenylphosphino)propane (95 mg, catalytic amount), palladium(II)acetate (48 mg, catalytic amount) and DMF/MeOH (30 mL, 3:1) were mixed in a 50 mL three necked round bottom flask. The flask was evacuated followed by the inlet of CO (repeated two times). The reaction mixture was stirred at 70° C. for 7.5 hours. The solvent was removed in vacuo and the residue was dissolved in diethyl ether/sat. $NaHCO_3$. The layers were separated and the water phase was extracted once with ether. The combined ether layers were dried ($MgSO_4$) and the solvent was removed in vacuo to give a crude which was purified by flash chromatography ($SiO_2$, hexane/EtOAC, 9:1) to give 1.3 g of the title compound (71% yield).

b) (R)-8-Fluoro-3-(N-isopropyl-N-n-propylamino)-5-carbamoyl-3,4-dihydro-2H-1-benzopyran Methyl (R)-8-Fluoro-3-(N-isopropyl-N-n-propylamino)-3,4-dihydro-2H-1-benzopyran-5-carboxylate (1.3 g, 4.2 mmol) and KOH (0.52 g, 8.4 mmol) were mixed in methanol (6 mL) and refluxed for 2.5 hours. The solvent was removed in vacuo. The residue was dissolved in water and made acidic by the addition of 2M HCl. The solvent was removed in vacuo. The residue was dissolved in $SOCl_2$ (30 mL) and refluxed for 2.5 hours. The solvent was removed in vacuo. The residue was dissolved in $CH_2Cl_2$ and the solvent was removed in vacuo again (repeated three times in order to remove the excess of $SOCl_2$. The residue was then dissolved in diethyl ether (50 mL). The solution was cooled to –30° C. before $NH_3$ (g) was bubbled through it. Water was added, the layers were separated and the water-phase was extracted with ether. The combined ether layers were dried ($K_2CO_3$) and the solvent was removed in vacuo to give a crude which was purified by flash chromatography ($SiO_2$, EtOAc/hexane, 1:1) to give 1.0 g of the title compound (yield 80%). Recrystallization from EtOAc/hexane gave crystals with Mp: 139°–140° C.

EXAMPLE 3

(R)-3-(N-tert-Butyl-N-n-propylamino)-5-carbamoyl-8-fluoro-3,4-dihydro-2H-1-benzopyran a) (R)-8-Fluoro-5-methoxy-3-[N-(4-methoxybenzylidene)-amino]-3,4-dihydro-2H-1-benzopyran (R)-3-Amino-8-fluoro-5-methoxy-3,4-dihydro-2H-1-benzopyran (7.85 g, 39.8 mmol), 4-methoxybenzaldehyde (5.42 g, 39.8 mmol), anhydrous potassium carbonate (10.1 g) and absolute EtOH (200 mL) were stirred over night at reflux temperature. The solvent was evaporated in vacuo and ether (500 mL) was added. After stirring for 15 min the salt was filtered off and the solution was concentrated in vacuo to give an off-white solid (12.4 g). Recrystallization from i-$Pr_2O$- hexane gave 10.8 g (86% yield) of the title compound as colourless needles. Mp: 96.8°–97.3° C.

$[\alpha]^{21}_D$=+20.1° (C=1; CHCl3) GC-MS (70 eV) M=315 (58%).

b) (R)-8-Fluoro-3-hydroxylamino-5-methoxy-3,4-dihydro- 2H -1-benzopyran

3-Chloroperoxybenzoic acid (85%; 7.6 g, 37.6 mmol) was added in portions to a stirred and cooled solution (+4° C.) of (R)-8-fluoro-5-methoxy-3-[N-(4-methoxybenzylidene)-amino]-3,4-dihydro-2H-1-benzopyran (10.8 g, 34 mmol) and methylene chloride (65 mL). The mixture was stirred over night at room temperature. Precipitated 3-chlorobenzoic acid was filtered off and the clear yellow filtrate was concentrated in vacuo. The oily residue was taken up in a solution of hydroxylamine hydrochloride (2.83 g, 40.8 mmol) and anhydrous methanol (60 mL) and the resulting solution was stirred at room temperature for 2 h. The solvent was evaporated to give a thick orange oil. Water was added to the oil, pH was adjusted to 8–9 with saturated aqueous $Na_2CO_3$ and the mixture was washed with ether (3×150 mL). The organic phases were combined, washed with brine, dried ($Na_2SO_4$), filtered and concentrated in vacuo. The crude product was flash chromatographed on silica with EtOAc (15 to 50%) in hexane as eluent. The resulting impure product was flash chromatographed a second time on silica with EtOH- $CHCl_3$ (1:99) as eluent to give 6.45 g (89% yield) of the title compound as a colourless crystalline solid. Mp: 111°–113° C. $[\alpha]^{21}_D=+66.4°$ (C=1.3; $CHCl_3$). GC-MS (70 eV) M=213 (56%).

c) (R)-3-tert-Butylamino-8-fluoro-5-methoxy-3,4-dihydro-2H-1-benzopyran (R)-8-Fluoro-3-hydroxylamino-5-methoxy-3,4-dihydro-2H-1-benzopyran (6.30 g, 29.6 mmol), anhydrous sodium sulfate (20 g) and acetone (500 mL) were refluxed under nitrogen for 4 days until TLC indicated a complete reaction. The salt was filtered off, ether (300 mL) was added to the filtrate and the solution, still containing finely suspended salt, was filtered through a sintered glass filter (grade 4). The clear filtrate was concentrated in vacuo. Dry (sieves 3 Å) benzene (50 mL) was added and the resulting solution was concentrated in vacuo (finally on the pump). The glassy residue was dissolved in dry (sieves 3 Å) benzene (150 mL) under nitrogen and the solution was cooled on an ice-bath (+4° C.). MeMgBr in $Et_2O$ (3.0M; 32.0 mL, 96 mmol) was added to the stirred solution above at a rate that kept the internal temperature below +5° C. (the reaction is exothermic). After the addition was complete (30 min) the solution was stirred at +4° C. for 0.5 h. The cooling bath was taken away and 15 min later the solution was poured on saturated $NaHCO_3$ and ice (300 mL total). The mixture was washed repeatedly with ether (3×150 mL). The organic phases were combined, washed with brine, dried ($Na_2SO_4$), filtered and concentrated in vacuo. Flash chromatography on silica [eluent: EtOAc (2 and 10%) in $CHCl_3$] gave 2.9 g. of the tert-butyl hydroxylamine derivative. The latter was dissolved in $CS_2$ (100 mL) under nitrogen and the solution was stirred at room temperature for 4.5 h. The solvent was evaporated in vacuo to give an orange oil. Acetone (approx. 50 mL) was added and the solution was stirred for a short time (15 min) at room temperature (to precipitate elemental sulfur), then filtered and concentrated to give an oil. Flash chromatography on silica [eluent: EtOAc (10 to 25%) in hexane] gave 2.34 g (31% total yield) of the title compound as a yellow oil. $[\alpha]^{21}_D=-82.8°$ (C=1; CHCl3). GC-MS (70 eV) M=253 (53%).

d) (R)-3-(N-tert-Butyl-N-n-propylamino)-8-fluoro-5-methoxy-3,4-dihydro-2H-1-benzopyran (R)-3-tert-Butylamino-8-fluoro-5-methoxy-3,4-dihydro-2H-1-benzopyran (2.20 g, 8.7 mmol), allyl bromide (7.5 mL, 87 mmol), finely ground anhydrous potassium carbonate (6.0 g, 43 mmol) and dry DMF (6.0 mL) were stirred under nitrogen at 65° C. After 70 h GC-analysis indicated partial conversion of the starting material (67% product vs. 30% starting material). At this stage the reaction was interrupted. The salt was sucked off, washed with a small portions of DMF and the clear filtrate was concentrated. The oil thus obtained was partitioned between saturated aqueous $Na_2CO_3$ and diethyl ether (4×70 mL). The organic phases were combined, washed with brine, dried ($MgSO_4$), filtered and concentrated in vacuo. Flash chromatograpy on silica [eluent: acetone (2 and 15%) in hexane] gave 0.80 g of starting material and 1.47 g (87% yield based on recovered starting material) of the allylated product as a colourless oil $[\alpha]^{21}_D=-77.6°$ (C=0.8 $CHCl_3$). GC-MS (70 eV) M=293 (40%). The allylated product (1.30 g) was mixed with DMF (50 mL) and 5% Rh on alumina (0.090 g) and hydrogenated at ambient pressure and temperature (21° C.). After 5 h the reaction was complete according to GC and TLC. The catalyst was filtered off on Celite, the pad was washed with small portions of DMF and the filtrate was concentrated in vacuo. Flash chromatography on silica of the crude product [eluent: EtOAc (0 and 3%) in $CH_2Cl_2$] gave 1.27 g (97% yield) of the saturated compound. GC-MS (70 eV) M=295 (28%). $[\alpha]^{21}_D$ (base)=-83.4° (C=0.9; CHCl3).

The base was dissolved in dry diethyl ether, the solution was cooled on an ice bath and an excess of ethereal HCl was added to the stirred solution. The salt was filtered off, washed with dry diethyl ether and dried in vacuo at 50° C. to give 1.39 g (98% yield) of the title compound, as white crystals. Mp: 175°–176° C.

e) (R)-3-(N-tert-Butyl-N-n-propylamino)-8-fluoro-5-hydroxy-3,4-dihydro-2H-1-benzopyran (R)-3-(N-tert-Butyl-N-n-propylamino)-8-fluoro-5-methoxy-3,4-dihydro-2H-1-benzopyran hydrochloride (1.3 g, 3.9 mmol) in dry methylene chloride (40 mL) under nitrogen was cooled on a dry ice-EtOH bath to −50° C. Boron tribromide (0.75 mL, 7.8 mmol) was added dropwise (in 1 min) to the stirred solution above. Five minutes after the addition of boron tribromide was complete, the dry-ice bath was changed to an ice bath (+4° C). After stirring for 4 h at the same temperature the solution was poured on ice (100 g) and solid $NaHCO_3$ was added to adjust pH to 8–9. When the ice had melted the mixture was extracted with ether (4×75 mL). The ether extracts were combined, washed with brine, dried ($Na_2SO_4$), filtered and concentrated in vacuo to afford 1.1 g (96% yield) of the title compound as a pale yellow oil. $[\alpha]^{21}_D=-91.7°$ (C=10; CHCl3) GC-MS (70 eV) M=281 (6%).

f) (R)-3-(N-tert-Butyl-N-n-propylamino)-8-fluoro-5-trifluoromethylsulfonyloxy-3,4-dihydro-2H-1-benzopyran (R)-3-(N-tert-Butyl-N-n-propylamino)-8-fluoro-5-hydroxy-3,4-dihydro-2H-1-benzopyran (1.0 g, 3.6 mmol) and 2,4,6-collidine (0.52 mL, 3.9 mmol) were dissolved in anhydrous methylene chloride (40 mL) and cooled to 30° C. Trifluoromethanesulfonic anhydride (0.66 mL, 3.9 mmol) dissolved in anhydrous methylene chloride (10 mL) was added dropwise during 20 min. The solution was allowed to warm to ambient temperature and after coming to 0° C. the reaction was done. The reaction was diluted with methylene chloride and washed with saturated aqueous $NaHCO_3$ (50 mL). The aqueous phase was re-extracted with ether (2×40 mL). The combined organic phases were dried ($MgSO_4$), filtered, and concentrated in vacuo to give a crude residue. Flash chromatography on silica [eluent: EtOAc-hexane (3:97)] gave 1.40 g (95% yield) of the title compound as a colourless oil. $[\alpha]^{21}_D=-73.7°$ (C=1.1; CHCl3). GC-MS (70 eV) M=413 (1%).

g) Methyl (R)-3-(N-tert-Butyl-N-n-propylamino)-8-fluoro-3,4-dihydro-2H-1-benzopyran-5-carboxylate (R)-3-(N-tert-Butyl-N-n-propylamino)-8-fluoro-5-trifluoromethylsulfonyloxy-3,4-dihydro-2H-1-benzopyran (1.4 g, 3.3 mmol) and triethylamine (1.0 mL, 7.4 mmol) were dissolved in a solution of DMF/MeOH (6:2; 30 mL) and then degassed followed by the inlet of carbon monoxide (4×). With a slight positive pressure of carbon monoxide, palladium(II)-acetate (0.030 g) and 1,3-bis(diphenylphosphino)propane (0.060 g) were added and the reaction mixture was degassed and subjected to carbon monoxide once again. The reaction was heated to 70° C. (oil-bath temperature) under carbon monoxide atmosphere with vigorous stirring for 12 h. GC indicating an incomplete reaction (68% product vs. 21% starting material), the solution was cooled and then filtered through Celite. More palladium(II)-acetate (0.030 g) and 1,3-bis(diphenylphosphino)propane (0.060 g) were added and the reaction was resumed as described above. After another 3 h GC indicated a slight improvement of the ratio (77% vs. 12%) and the reaction was allowed to cool. The following day the solvent was removed in vacuo. The remaining red-brown oil was taken into saturated aqueous $NaHCO_3$ and then extracted with EtOAc (3×50 mL). The combined organic phases were washed with brine, dried ($MgSO_4$), filtered and concentrated in vacuo to give the crude ester. Flash chromatography on silica [eluent: EtOAc (15 and 30%) in hexane] gave 0.178 g of starting material and 0.842 g (89% yield based on recovered starting material) of the title compound as a clear oil. $[\alpha]^{21}_D=-121.1°$ (C=0.9; CHCl3). GC-MS (70 eV) M=323 (14%).

h) (R)-3-(N-tert-Butyl-N-n-propylamino)-5-carbamoyl-8-fluoro-3,4-dihydro-2H-1-benzopyran Methyl (R)-3-(N-tert-butyl-N-n-propylamino)-8-fluoro-3,4-dihydro-2H-1-benzopyran-5-carboxylate (0.84 g, 2.6 mmol), methanol (10 mL) and 1.7M aqueous NaOH (3.0 mL, 5.2 mmol) were refluxed for 3 h. The clear solution was cooled, the methanol was stripped, the aqueous remains were washed twice with ether-hexane (1:1), then acidified with 2M HCl (pH<2). The water was evaporated in vacuo and the remaining salt was dried in vacuum at 50° C. for 2 h. Dry methylene chloride (20 mL) and thionyl chloride (3.0 mL, 41 mmol) were added, the mixture refluxed under nitrogen for 11 h. The volatiles were evaporated, more dry methylene chloride was added and evaporated. This was repeated once. The crude acid chloride was dissolved (suspended) in dry methylene chloride (50 mL) and added dropwise to stirred concentrated aqueous ammonia (40 mL) cooled on an ice bath. The mixture was allowed to warm to ambient temperature, the organic phase was separated, and the aqueous phase was washed with methylene chloride (100 mL) and ether (50 mL). The organic portions were combined, dried ($MgSO_4$), filtered and concentrated to give the crude amide. Flash chromatography on silica [eluent: EtOAc-hexane (4:5)]) gave 0.73 g (91% yield) of (R)-3-(N-tert-butyl-N-propylamino)-8-fluoro-3,4-dihydro-2H-1-benzopyran-5-carboxamide as a solid. Mp: 70°–75° C. $[\alpha]^{21}_D=-132.4°$ (C=1.0; CHCl3). GC-MS (70 eV) M=308 (3%).

The base was dissolved in dry ether, the solution was cooled on a dry-ice bath (−20° C.) and an excess of ethereal HCl was added to the stirred solution. The salt was filtered off, washed with dry ether and dried in vacuo at 50° C. to give 0.78 g (96% yield) of the hydrochloride salt as white crystals. Mp: 120° C. sinters.

EXAMPLE 4

(R)-5-Carbamoyl-3-(N,N-dicyclobutylamino)-8-fluoro-3,4-dihydro-2H-1-benzopyran a) (R)-3-(N-Cyclobutylamino)-8-fluoro-5-methoxy-3,4-dihydro-2H-1-benzopyran and

(R)-3-(N,N-Dicyclobutylamino)-8-fluoro-5-methoxy-3,4-dihydro-2H-1-benzopyran (R)-3-Amino-8-fluoro-5-methoxy-3,4-dihydro-2H-1benzopyran (1.67 g, 8.47 mmol) was dissolved in anhydrous methanol (20 mL) and to this was cyclobutanone (5.0 g, 71.3 mmol) added. The reaction was cooled (ice-bath) then sodium cyanoborohydride (0.96 g, 15.3 mmol) was added and the reaction was allowed to stir at room temperature overnight. After 24 h the pH was adjusted to 4–5 with acetic acid and the reaction was allowed to stir for one more day. The solvent was removed in vacuo, the remains were were dried ($Na_2SO_4$) filtered, and the solvent removed taken into a 2M solution of $NH_3$ and then extracted thrice with diethyl ether. The combined ether portions in vacuo to give the crude residue. Chromatography on silica (eluent: 15% ethyl acetate/hexane for dialkylated product followed by ethyl acetate for monoalkylated product) gave 1.01 g (48% yield) of the monoalkylated title compound as a clear oil [GC-MS (70 eV) M=251 (6%)]. and 0.71 g (27% yield) of the dialkylated title compound as a clear oil. $[\alpha]^{21}_D=-101.0°$ (C=0.1; CHCl3) GC-MS (70 eV) M=305 (3%).

b) (R)-8-Fluoro-3-(N,N-dicyclobutylamino)-5-hydroxy-3,4-dihydro-2H-1-benzopyran (R)-8-Fluoro-3-(N,N-dicyclobutylamino)-5-methoxy-3,4-dihydro-2H-1-benzopyran hydrochloride (0.77 g, 2.26 mmol) was dissolved in anhydrous $CH_2Cl_2$ (20 mL) and cooled to −40° C. To the solution was $BBr_3$ (0.54 mL, 5.7 mmol), dissolved in anhydrous $CH_2Cl_2$ (3 mL), added dropwise. The cooling-bath was removed and after 2 h at room temperature the reaction was completed. The reaction was poured out onto an ice/2M $NH_3$ solution and the mixture was extracted, twice, with ($MgSO_4$), filtered, and the solvent removed in vacuo to diethyl ether. The combined ether portions were dried give the crude residue. Chromatography on silica (eluent: 50% ethyl acetate/hexane) gave 0.58 g (89% yield) of the title compound as a white solid. Mp: 170°–2° C. $[\alpha]^{21}_D=-114.4°$ (C=0.1; CHCl3) GC-MS (70 eV) M=291 (2%).

c) (R)-3-(N,N-Dicyclobutylamino)-8-fluoro-5-trifluoromethylsulfonyloxy-3,4-dihydro-2H-1-benzopyran (R)-3-(N,N-Dicyclobutylamino)-8-fluoro-5-hydroxy-3,4-dihydro-2H-1-benzopyran (0.59 g, 2.02 mmol) and collidine (0.37 mL, 2.8 mmol) were dissolved in anhydrous $CH_2Cl_2$ (40 mL) and cooled to −40° C. Trifluoromethanesulfonic anhydride (0.41 mL, 2.4 mmol) was added dropwise and allowed to warm to ambient temperature, and after coming to 0° C. the reaction was done. The reaction was diluted with $CH_2Cl_2$ and washed with a saturated aqueous $NaHCO_3$ solution, dried ($MgSO_4$), filtered, and evaporated in vacuo to give a crude residue. Chromatography on silica (eluent: $CH_2Cl_2$) gave 0.84 g (99% yield) of the title compound as a clear oil. $[\alpha]^{21}_D=-90.9°$ (C=0.1; CHCl3) GC-MS (70 eV) M=423 (3%).

Methyl (R)-3-(N,N-Dicyclobutylamino)-8-fluoro-3, 4-dihydro-2H-1-benzopyran-5-carboxylate (R)-3-(N,N-Dicyclobutylamino)-8-fluoro-5-trifluoromethylsulfonyloxy-3,4-dihydro-2H-1-benzopyran (0.82 g, 1.94 mmol) was dissolved in a solution of DMF/methanol (6:2, 15 mL) and then degassed followed by the inlet of carbonmonoxide (×3). With a slight positive pressure of carbonmonoxide, palladium(II)-acetate (14 mg), 1,3-bis-(diphenylphosphino)propane (25 mg) and triethylamine (0.60 mL, 4.3 mmol) were added and the reaction mixture was degassed and subjected to carbonmonoxide once again. The reaction was heated to 70° C. under carbonmonoxide atmosphere with vigorous stirring for 5.5 h. The reaction was allowed to cool and the solvent was removed in vacuo. The remains were taken into a 2M solution of $NH_3$ and then extracted, twice, with diethyl ether. The combined ether portions were dried ($MgSO_4$), filtered, and the solvent removed in vacuo to give the crude residue. Chromatography on silica (eluent: 12.5% ethyl acetate/hexane) gave 501 mg (78% yield) of the title compound as a clear oil. $[\alpha]^{21}_D=-138.2°$ (C=0.1; CHCl3) GC-MS (70 eV) M=333 (4%).

e) (R)-5-Carbamoyl-3-(N,N-dicyclobutylamino)-8-fluoro-3,4-dihydro-2H-1-benzopyran Methyl (R)-3-(N,N-dicyclobutylamino)-8-fluoro-3,4-dihydro-2H-1-benzopyran-5-carboxylate (490 mg, 1.47 mmol) was refluxed with a 6M solution of HCl (20 mL) for 3.5 h. The solution was cooled, concentrated to dryness in vacuo and anhydrous toluene was added and the solvent was removed in vacuo (×4). To the white solid was thionyl chloride (15 mL) added and the solution was allowed to stir at room temperature overnight. The excess thionyl chloride was removed in vacuo, anhydrous toluene added and the solvent removed in vacuo.

The acid chloride was dissolved in $CH_2Cl_2$ (20 mL) and added dropwise to a cooled solution (ice-bath) of concentrated $NH_3$ (20 mL). The reaction was allowed to stir at room temperature for 30 min. The $CH_2Cl_2$ phase was separated and the aqueous portion was re-extracted with $CH_2Cl_2$ (×3). The combined $CH_2Cl_2$ portions were dried ($MgSO_4$), filtered, and evaporated in vacuo to give the crude residue. Chromatography on silica (eluent: ethyl acetate) gave 430 mg (92% yield) of a white solid. Mp: 141.2°–142.2° C. $[\alpha]^{21}_D=-151.5°$ (C=0.1; CHCl3) GC-MS (70 eV) M=318 (3%).

The hydrochloride salt was made by dissolving the pure base in ether and dropping an excess of an ethereal HCl solution. The salt was washed with diethyl ether to give a white solid. Mp: 120° C. sinters.

EXAMPLE 5

(R)-5-Carbamoyl-3-N-cyclobutyl-N-n-propylamino)-8-fluoro-3,4-dihydro-2H-1-benzoxpyran a) (R)-3-(N-Cyclobutyl-N-n-propylamino)-8-fluoro-5-methoxy-3,4-dihydro-2H-1-benzopyran (R)-3-(N-Cyclobutylamino)-8-fluoro-5-methoxy-3,4-dihydro-2H-1-benzopyran (1.01 g, 4.02 mmol) was dissolved in anhydrous methanol (20 mL) and to this was n-propionaldehyde (3.0 mL, 40.2 mmol) added. After 1 h the reaction was cooled (ice-bath) then sodium cyanoborohydride (0.46 g, 7.24 mmol) was added, the pH was adjusted to 4–5 with acetic acid and the reaction was allowed to stir at room temperature over the weekend. The solvent was removed in vacuo, the remains extracted thrice with diethyl ether. The combined ether portions were dried ($MgSO_4$) filtered, and the solvent were taken into a 2M solution of $NH_3$ and then removed in vacuo to give the crude residue. Chromatography on silica (eluent: 11% ethyl acetate/hexane) gave 0.95 g (80% yield) of the title compound as a clear oil. $[\alpha]^{21}_D=-95.4°$ (C=0.1; CHCl3) GC-MS (70 eV) M=293 (1%).

b) (R)-3-(N-Cyclobutyl-N-n-propylamino)-8-fluoro-5-hydroxy-3,4-dihydro-2H-1-benzopyran (R)-3-(N-Cyclobutyl-N-n-propylamino)-8-fluoro-5-methoxy-3,4-dihydro-2H-1 -benzopyran hydrochloride (1.0 g, 3.03 mmol) was dissolved in anhydrous $CH_2Cl_2$ (25 mL) and cooled to –40° C. To the solution was $BBr_3$ (0.72 mL, 7.6 mmol), dissolved in anhydrous $CH_2Cl_2$ (4 mL), added dropwise. The cooling-bath was removed and after 2 h at room temperature the reaction was complete. The reaction was poured out onto an ice/2M $NH_3$ solution and the $CH_2Cl_2$ portion was separated, the aqueous layer re-extracted, twice, with $CH_2Cl_2$. The combined $CH_2Cl_2$ portions were dried ($MgSO_4$), filtered, and the solvent removed in vacuo to give the crude residue. Chromatography on silica (eluent: 25% ethyl acetate/hexane followed by 50% ethyl acetate/hexane) gave 0.83 g (98% yield) of the title compound as a gum. $[\alpha]^{21}_D=-80.5°$ (C=0.1; CHCl3) GC-MS (70 eV) M=279 (0.2%).

c) (R)-3-(N-Cyclobutyl-N-n-propylamino)-8-fluoro-5-trifluoromethylsulfonyloxy-3,4-dihydro-2H-1-benzopyran (R)-3-(N-Cyclobutyl-N-n-propylamino)-8-fluoro-5-hydroxy-3,4-dihydro-2H-1-benzopyran (0.80 g, 2.86 mmol) and collidine (0.53 mL, 4.0 mmol) were dissolved in anhydrous $CH_2Cl_2$ (30 mL) and cooled to –40° C. Trifluoromethanesulfonic anhydride (0.60 mL, 3.6 mmol) was added dropwise and allowed to warm to ambient temperature, and after coming to 0° C. the reaction was done. The reaction was diluted with $CH_2Cl_2$ and washed with a saturated aqueous $NaHCO_3$ solution, the aqueous was re-extracted, twice, with $CH_2Cl_2$ the combined $CH_2Cl_2$ portions were dried ($MgSO_4$), filtered, and evaporated in vacuo to give a crude residue. Chromatography on silica (eluent: $CH_2Cl_2$) gave 1.01 g (86% yield) of the title compound as a clear oil. $[\alpha]^{21}_D=-78.6°$ (C=0.1; CHCl3) GC-MS (70 eV) M=411 (1%).

d) Methyl (R)-3-(N-Cyclobutyl-N-n-propylamino)-8-fluoro-3,4-dihydro-2H-1-benzopyran-5-carboxylate (R)-3-(N-Cyclobutyl-N-n-propylamino)-8-fluoro-5-trifluoromethylsulfonyloxy-3,4-dihydro-2H-1-benzopyran (1.00 g, 2.43 mmol) was dissolved in a solution of DMF/methanol (6:2, 20 mL) and then degassed followed by the inlet of carbonmonoxide (×3). With a slight positive pressure of carbonmonoxide, palladium(II)-acetate (18 mg), 1,3-bis(diphenylphosphino)propane (25 mg) and triethylamine (0.75 mL, 5.3 mmol) were added and the reaction mixture was degassed and subjected to carbonmonoxide once again. The reaction was heated to 70° C. under carbonmonoxide atmosphere with vigorous stirring for 6 h. The reaction was allowed to cool and the solvent was removed in vacuo. The remains were taken into a 2M solution of $NH_3$ and then extracted, twice, with diethyl ether. The combined ether portions were dried (MgSO₄), filtered, and the solvent removed in vacuo to give the crude residue. Chromatography on silica (eluent: 15% ethyl acetate/hexane) gave 0.73 mg (94% yield) of the title compound as a clear oil. $[\alpha]^{21}_D = -130.1°$ (C=0.1; CHCl3) GC-MS (70 eV) M=321 (2%).

e) (R)-5-Carbamoyl-3-(N-cyclobutyl-N-n-propylamino)-8-fluoro-3,4-dihydro-2H-1-benzopyran Methyl (R)-3-(N-cyclobutyl-N-n-propylamino)-8-fluoro-3,4-dihydro-2H-1-benzopyran-5-carboxylate (0.71 mg, 2.21 mmol) was refluxed with a 6M solution of HCl (30 mL) for 3.5 h. The solution was cooled, concentrated to dryness in vacuo and anhydrous toluene was added and the solvent was removed in vacuo (×4). To the white solid was thionyl chloride (20 mL) added and the solution was allowed to stir at room temperature overnight. The excess thionyl chloride was removed in vacuo, anhydrous toluene added and the solvent removed in vacuo. The acid chloride was dissolved in CH₂Cl₂ (30 mL) and added dropwise to a cooled solution (ice-bath) of concentrated NH₃ (30 mL). The reaction was allowed to stir at room temperature for 40 min. The CH₂Cl₂ phase was separated and the aqueous portion was re-extracted with CH₂Cl₂ (×3). The combined CH₂Cl₂ portions were dried (MgSO₄), filtered, and evaporated in vacuo to give the crude residue. Chromatography on silica (eluent: ethyl acetate) gave 622 mg (92% yield) of a white semicrystalline solid. A portion was recrystallized from ethyl acetate/hexane to give a feathery white solid. Mp: 107°–9° C. $[\alpha]^{21}_D = -133.0°$ (C=0.1; CHCl3) GC-MS (70 eV) M=306 (0.5%).

EXAMPLE 6

(R)-5-Carbamoyl-3-(N-cyclobutyl-N-isoproylamino)-8-fluoro-3,4-dihydro-2H-1-benzopyran a) (R)-8-Fluoro-3-(N-isopropylamino)-5-methoxy-3,4-dihydro-2H-1-benzopyran (R)-3-Amino-8-fluoro-5-methoxy-3,4-dihydro-2H-1-benzopyran (1.62 g, 8.21 mmol) was dissolved in anhydrous methanol (20 mL) and to this was acetone (6.0 mL, 82.1 mmol) added. The reaction was cooled (ice-bath) then sodium cyanoborohydride (0.92 g, 14.8 mmol) was added, the pH was adjusted to 4–5 with acetic acid and the reaction was allowed to stir at room temperature overnight. The solvent was removed in vacuo, the remains were taken into a 2M solution of NH₃ and then extracted thrice with diethyl ether. The combined ether portions were dried (MgSO₄), filtered, and the solvent removed in vacuo to give the crude residue that was used as is in the next reaction. GC-MS (70 eV) M=239 (81%).

b) (R)-3-(N-Cyclobutyl-N-isopropylamino)-8-fluoro-5-methoxy-3,4-dihydro-2H-1-benzopyran (R)-8-Fluoro-3-(N-isopropylamino)-5-methoxy-3,4-dihydro-2H-1-benzopyran (1.96 g, 8.19 mmol) was dissolved in anhydrous methanol (20 mL) and to this was cyclobutanone (6.1 mL, 81.9 mmol) added. The reaction was cooled (ice-bath) then sodium cyanoborohydride (2.0 g, 16.4 mmol) was added, the pH was adjusted to 4–5 with acetic acid, 3 Å molecular sieves were added and the reaction was allowed to stir at room temperature overnight. After 24 h the pH was again adjusted to 4–5 and the reaction was allowed to stir for 3 more days. The reaction was filtered, solvent was removed in vacuo, the remains were taken into a 2M solution of NH₃ and then extracted thrice with diethyl ether. The combined ether portions were dried (MgSO₄) filtered, and the solvent removed in vacuo to give the crude residue. Chromatography on silica (eluent: 10% ethyl acetate/hexane) gave 1.60 g (77% yield) of the title compound as a clear oil. $[\alpha]^{21}_D = -95.1°$ (C=0.1; CHCl3). GC-MS (70 eV) M=293 (3%).

c) (R)-3-(N-Cyclobutyl-N-isopropylamino)-8-fluoro-5-hydroxy-3,4-dihydro-2H-1-benzopyran (R)-3-(N-Cyclobutyl-N-isopropylamino)-8-fluoro-5-methoxy-3,4-dihydro-2H-1-benzopyran hydrochloride (1.76 g, 5.34 mmol) was dissolved in anhydrous CH₂Cl₂ (45 mL) and cooled to −40° C. To the solution was BBr₃ (1.3 mL, 13.4 mmol), dissolved in anhydrous CH₂Cl₂ (7 mL), added dropwise. The cooling-bath was removed and after 2 h at room temperature the reaction was complete. The reaction was poured out onto an ice/2M NH₃ solution and the CH₂Cl₂ portion was separated, the aqueous layer re-extracted, twice, with CH₂Cl₂. The combined CH₂Cl₂ portions were dried (MgSO₄), filtered, and the solvent removed in vacuo to give the crude residue. Chromatography on silica (eluent: 30% ethyl acetate/hexane) gave 1.46 g (98% yield) of the title compound as a gum $[\alpha]^{21}_D = -95.7°$ (C=0.1; CHCl3) GC-MS (70 eV) M=279 (0.7%). The hydrochloride salt was made by dissolving the pure base in ether and dropping an excess of an ethereal HCl solution. The salt was washed with diethyl ether to give a white solid Mp: 120° C. sinters.

d) (R)-3-(N-Cyclobutyl-N-isopropylamino)-8-fluoro-5-trifluoromethylsulfonyloxy-3,4-dihydro-2H-1-benzopyran (R)-3-(N-Cyclobutyl-N-isopropylamino)-8-fluoro-5-hydroxy-3,4-dihydro-2H-1-benzopyran (1.36 g, 4.87 mmol) and collidine (0.90 mL, 6.8 mmol) were dissolved in anhydrous CH₂Cl₂ (50 mL) and cooled to −40° C. Trifluoromethanesulfonic anhydride (1.05 mL, 6.1 mmol) was added dropwise and allowed to warm to ambient temperature, and after coming to 0° C. the reaction was done. The reaction was diluted with CH₂Cl₂ and washed with a saturated aqueous NaHCO₃ solution, the aqueous was re-extracted, twice, with CH₂Cl₂ the combined CH₂Cl₂ portions were dried (MgSO₄), filtered, and evaporated in vacuo to give a crude residue. Chromatography on silica (eluent: 70% hexane/CH₂Cl₂) gave 1.67 g (83% yield) of the title compound as a slightly yellow oil. $[\alpha]^{21}_D = -86.8°$ (C=0.1; CHCl3). GC-MS (70 eV) M=411 (0.3%).

e) Methyl (R)-3-(N-Cyclobutyl-N-isopropylamino)-8-fluoro-3,4-dihydro-2H-1-benzopyran-5-carboxylate (R)-3-(N-Cyclobutyl-N-isopropylamino)-8-fluoro-5-trifluoromethylsulfonyloxy-3,4-dihydro-2H-1-benzopyran (1.65 g, 4.01 mmol) was dissolved in a solution of DMF/methanol (6:2, 30 mL) and then degassed followed by the inlet of carbonmonoxide (×3). With a slight positive pressure of carbonmonoxide, palladium(II)-acetate (30 mg), 1,3-bis(diphenylphosphino)propane (55 mg) and triethylamine (1.25 mL, 8.8 mmol) were added and the reaction mixture was degassed and subjected to carbonmonoxide once again. The reaction was heated to 70° C. under carbonmonoxide atmosphere with vigorous stirring for 6 h. The reaction was allowed to cool and the solvent was ether. The combined ether portions were dried (MgSO₄), removed in vacuo. The remains were taken into a 2M solution of NH₃ and then extracted, twice, with diethyl filtered, and the solvent removed in vacuo to give the crude residue. Chromatography on silica (eluent: 8% ethyl acetate/hexane) gave 1.18 mg (92% yield) of the title compound as a clear oil. $[\alpha]^{21}_D = -139.1°$ (C=0.1; CHCl3) GC-MS (70 eV) M=321 (3%).

f) (R)-5-Carbamoyl-3-(N-cyclobutyl-N-isopropylamino)-8-fluoro-3,4-dihydro-2H-1-benzopyran Methyl (R)-3-(N-cyclobutyl-N-isopropylamino)-8-fluoro-3,4-dihydro-2H-1-benzopyran-5-carboxylate (1.16 mg, 3.61 mmol) was refluxed with a 6M solution of HCl (30 mL) for 3.5 h. The solution was cooled, concentrated to dryness in vacuo and anhydrous toluene was added and the solvent was removed in vacuo (×4). To the white gum was thionyl chloride (35 mL) added and the solution was allowed to stir at room temperature overnight. The excess thionyl chloride was removed in vacuo, anhydrous toluene added and the solvent removed in vacuo. The acid chloride was dissolved in $CH_2Cl_2$ (50 mL) and added dropwise to a cooled solution (ice-bath) of concentrated $NH_3$ (50 mL). The reaction was allowed to stir at room temperature for 40 min. The $CH_2Cl_2$ phase was separated and the aqueous portion was re-extracted with $CH_2Cl_2$ (×3). The combined $CH_2Cl_2$ portions were dried ($MgSO_4$), filtered, and evaporated in vacuo to give the crude residue. Chromatography on silica (eluent: ethyl acetate) gave 1.06 g (95% yield) of a white foam. The foam was crystallized using $CH_2Cl_2$/ hexane to give a white solid. Mp: 127.8°–128.4° C. $[\alpha]^{21}_D = -143.0°$ (C=0.1; CHCl3) GC-MS (70 eV) M=306 (0.3%).

The hydrochloride salt was made by dissolving the pure base in ether and dropping an excess of an ethereal HCl solution. The salt was washed with diethyl ether to give a white solid. Mp: 120° C. sinters.

EXAMPLE 7

(R)-5-Carbamoyl-3-(N-cyclopentyl-N-n-propylamino)-8-fluoro-3,4-dihydro-2H-1-benzopyran a) (R)-3-(N-Cyclopentylamino)-8-fluoro-5-methoxy-3,4dihydro-2H-1-benzopyran To a solution of (R)-3-amino-8-fluoro-5-methoxy-3,4-dihydro-2H-1-benzopyran (2.5 g, 12 mmol), cyclopentanone (3.3 g, 36 mmol) and HOAc (0.7 g, 12 mmol) in methanol (25 mL) was $NaCNBH_3$ (2.5 g, 40 mmol) added in portions at room temperature. The solution was stirred at room temperature overnight to give a quantitative yield of the title compound. GC/MS (70 eV) M=265 (30%).

b) (R)-3-(N-Cyclopentyl-N-n-propylamino)-8-fluoro-5-methoxy-3,4-dihydro-2H-1-benzopyran To the solution of (R)-3-(N-cyclopentylamino)-8-fluoro-5-methoxy-3,4-dihydro-2H-1-benzopyran in methanol (25mL) were propanal (2 g, 36 mmol) and $NaCNBH_3$ (2 g, 40 mmol) added. The solution was stirred overnight to give the desired compound in a 97% yield according to GC. The solvent was removed in vacuo and the residue was worked up by extraction to give 3.7 g of the title compound as a colorless oil. GC/MS (70 eV) M=307 (40% ).

c) (R)-3-(N-Cyclopentyl-N-n-propylamino)-8-fluoro-5-hydroxy-3,4-dihydro-2H-1-benzopyran The HCl salt of (R)-3-(N-cyclopentyl-N-n-propylamino)-8-fluoro-5-methoxy-3,4-dihydro-2-H-1-benzopyran was prepared by adding an excess of an ethereal HCl into an ethereal solution of the base. The solvent was evaporated in vacuo and the residue dissolved in 48% aqueous HBr (50 mL). The solution was stirred at 120° C. for 1.5 h. The solution was neutralized by carefully adding conc. ammonia. Extractive work-up gave a brown oil which was filtered through a plug of silica (ethyl acetate as the eluent). The title compound was isolated (3.7 g) as a slightly yellow oil. GC/MS (70 eV) M=293 (40%).

d) (R)-3-(N-Cyclopentyl-N-n-propylamino)-8-fluoro-5-trifluoromethylsulfonyloxy-3,4-dihydro-2H-1-benzopyran (R)-3-(N-Cyclopentyl-N-n-propylamino)-8-fluoro-5-hydroxy-3,4-dihydro-2H-1-benzopyran was dissolved in diethyl ether (100 mL). Triethylamine (3 g, 30 mmol) was added and the mixture was cooled to −20 ° C. Trifluoromethanesulfonic anhydride (4.2 g, 15 mmol), dissolved in diethyl ether (20 mL), was added dropwise (5 min). After stirring for 30 min, the dark-brownish mixture was poured into water. The organic layer was separated. Flash chromatography (ethyl acetate as the eluent) gave 3.7 g of the title compound as a yellow oil in a 69% yield. GC/MS (70 eV) M=425 (10%).

e) Methyl (R)-3-(N-Cyclopentyl-N-n-propylamino)-8-fluoro-3,4-dihydro-2H-1-benzopyran-5-carboxylate (R)-3-(N-Cyclopentyl-N-n-propylamino)-8-fluoro-5 -trifluoromethylsulfonyloxy-3,4-dihydro-2H-1-benzopyran (3.7 g, 8.7 mmol), DMF (50 mL), triethylamine (2.5 g, 25 mmol), methanol (4 g, 130 mmol), palladium(ll)acetate (100 mg, 0.45 mmol) and 1,3-bis(diphenylphosphino)propane (200 mg, 0.48 mmol) were placed in a round-bottomed flask. The solution was stirred at 75° C. in an atmosphere of carbon monoxide for 4 h. After evaporation of the solvent in vacuo and subjecting the crude to flash chromatography, 2.5 g (86% yield) of the title compound as a colorless oil was isolated. GC/MS (70 eV) M=335 (20 %).

f) (R)-5-Carbamoyl-3-(N-cyclopentyl-N-n-propylamino)-8-fluoro-3,4-dihydro-2H-1-benzopyran Methyl (R)-3-(N-cyclopentyl-N-n-propylamino) -8-fluoro-3,4-dihydro-2H-1-benzopyran-5-carboxylate (1.4 g, 4 mmol) was hydrolysed (6 M HCl, refluxed for 2 h) and the solvent was removed in vacuo. The crude acid was treated with $SOCl_2$ (room temperature for 5 min) to form the acid chloride which after removal of excess $SOCl_2$ in vacuo was added to conc. ammonia to form the amide. The crude product was isolated and purified by flash chromatography. The HCl salt was prepared by adding an excess of ethereal HCl into an ethereal solution of the pure base to afford the title compound (0.5 g, yield 35%) as white crystals. Mp: 85° C. dec. $[\alpha]^{20}_D$ (base)=−91° (C=0.2; $CH_2Cl_2$). GC/MS (70 eV) M=320 (25%).

EXAMPLE 8

(R)-5-Carbamoyl-3-(N-cyclohexyl-N-n-propylamino)-8-fluoro-3,4-dihydro-2H-1-benzopyran a) (R)-3-(N-Cyclohexylamino)-8-fluoro-5-methoxy-3,4-dihydro-2H-1-benzopyran To a solution of (R)-3-amino-8-fluoro-5-methoxy-3,4-dihydro-2H-1-benzopyran (0.45 g, 2.2 mmol), cyclohexanone (0.7 g, 7.2 mmol) and HOAc (0.14 g, 2.3 mmol) in methanol (25 mL) was $NaCNBH_3$ (0.5 g, 8 mmol) added in portions at room temperature. The solution was stirred at room temperature overnight to give a quantitative yield of the title compound. GC/MS (70 eV) M=279 (30%).

b) (R)-3-(N-Cyclohexyl-N-n-propylamino)-8-fluoro-5-methoxy-3,4-dihydro-2H-1-benzopyran To the solution of (R)-3-(N-cyclohexylamino)-8-fluoro-5-methoxy-3,4-dihydro-2H-1-benzopyran in methanol (25 mL) were propanal (1.3 g, 23 mmol) and NaCNBH$_3$ (0.15 g, 2.3 mmol) added. The solution was stirred overnight to give the desired compound in a 97% yield according to GC. The solvent was removed in vacuo and the residue was worked up by extraction to give 0.7 g of the title compound as a colorless oil. GC/MS (70 eV) M=321 (40%).

c) (R)-3-(N-Cyclohexyl-N-n-propylamino)-8-fluoro-5-hydroxy-3,4-dihydro-2H-1-benzopyran The HCl salt of the (R)-3-(N-cyclohexyl-N-n-propylamino)-8-fluoro-5-methoxy-3,4-dihydro-2-H-1benzopyran was prepared by adding an excess of an ethereal HCl into an ethereal solution of the base. The solvent was evaporated in vacuo and the residue dissolved in 48% aqueous HBr (20 mL). The solution was stirred at 120° C. for 1.5 h. The solution was neutralized by carefully adding conc. ammonia. Extractive work-up gave a brown oil which was filtered through a plug of silica (ethyl acetate as the eluent). The title compound was isolated (0.6 g) as a slightly yellow oil. GC/MS (70 eV) M=307 (40%).

d) (R)-3-(N-Cyclohexyl-N-n-propylamino)-8-fluoro-5-trifluoromethylsulfonyloxy-3,4-dihydro-2H-1-benzopyran (R)-3-(N-Cyclohexyl-N-n-propylamino)-8-fluoro-5-hydroxy-3,4-dihydro-2H-1-benzopyran was dissolved in diethyl ether (30 mL) and triethylamine (0.8 g, 8 mmol) was added and the mixture was cooled to −20 ° C. Trifluoromethanesulfonic anhydride (0.8 g, 2.8 mmol), dissolved in diethyl ether (10 mL), was added dropwise (5 min). After stirring for 30 min, the dark-brownish mixture was poured into water. The organic layer was separated. Flash chromatography (EtOAc/hexane 1+1 as the eluent) gave 0.8 g of the title compound as a yellow oil. GC/MS (70 eV) M=439 (20%).

e) Methyl (R)-3-(N-Cyclohexyl-N-n-propylamino)-8-fluoro-3,4-dihydro-2H-1-benzopyran-5-carboxylate (R)-3-(N-Cyclohexyl-N-n-propylamino)-8-fluoro-5-trifluoromethylsulfonyloxy-3,4-dihydro-2H-1-benzopyran (0.8 g, 1.8 mmol) (4), DMF (30 mL), triethylamine (0.5 g, 5 mmol), methanol (0.8 g, 13 mmol), palladium(II)acetate (30 mg, 0.14 mmol) and 1,3-bis(diphenylphosphino)propane (60 mg, 0.14 mmol) were placed in a round-bottomed flask. The solution was stirred at 75° C. in an atmosphere of carbon monoxide for 4 h. After evaporation of the solvent in vacuo and subjecting the crude to flash chromatography, 0.6 g (76% yield) of the title compound as a colorless oil was isolated. GC/MS (70 eV) M=349 (30 %).

f) (R)-5-Carbamoyl-3-(N-cyclohexyl-N-n-propylamino)-8-fluoro-3,4-dihydro-2H-1-benzopyran Methyl (R)-3-(N-cyclohexyl-N-n-propylamino)-8-fluoro-3,4-dihydro-2H-1-benzopyran-5-carboxylate (5) (0.6 g, 1.7 mmol) was subjected to alkaline hydrolysis (2% KOH in EtOH, refluxed for 2 h). The solvent was removed in vacuo and the crude acid was treated with SOCl$_2$ (room temperature for 5 min) to form the acid chloride which after removal of excess SOCl$_2$ in vacuo was added to conc. ammonia to form the amide. The crude product was isolated and purified by flash chromatography. The HCl salt was prepared by adding an excess of ethereal HCl into an ethereal solution of the pure base to afford the title compound (86 mg, yield 14%) as white crystals Mp: 75° C. dec [α]$^{20}_D$=−73° (C=0.2 CH$_2$Cl$_2$). GC/MS (70 eV) M=334 (35%).

EXAMPLE 9

(R)-5-Carbamoyl-3-(N-cyclopentyl-N-cyclobutylamino)-8-fluoro-3,4-dihydro-2H-1-benzopyran a) (R)-3-(N-Cyclopentylamino)-8-fluoro-5-methoxy-3,4-dihydro-2H-1-benzopyran To a solution of (R)-3-amino-8-fluoro-5-methoxy-3,4-dihydro-2H-1-benzopyran (0.7 g, 3.4 mmol), cyclopentanone (0.7 g, 8.3 mmol) and HOAc (0.2 g, 3.5 mmol) in methanol (25 mL), NaCNBH$_3$ (0.7 g, 10 mmol) was added in portions at room temperature. The solution was stirred at room temperature over night. The methanol was evaporated. The residue was dissolved in EtOAc and washed with water. The organic layer was dried with Na$_2$SO$_4$ and the solvent was evaporated to give 0.9 g (100% yield) of the title compound as a colourless oil. GC indicated 99.6 purity. GC/MS (70 eV) M=265 (30%).

b) (R)-3-(N-Cyclopentyl-N-cyclobutyl-amino)-8-fluoro-5-methoxy-3,4-dihydro-2H-1-benzopyran To a solution of (R)-3-(N-cyclopentylamino)-8-fluoro-5-methoxy-3,4-dihydro-2H-1-benzopyran (0.9 g, 3.4 mmol), HOAc (0.22 g, 3.6 mmol) and cyclobutanone (2g, 30 mmol) in methanol (25 mL), were NaCNBH$_3$ (1 g, 16 mmol) added in portions at room temperature. After stirring for four days GC indicated 37% product. pH was adjusted to 5 (HOAc)and additional (1 g, 15 mmol) cyclobutanone was added. After stirring for further 6 days, GC indicated 64% conversion. The solvent was evaporated and the residue worked up by extraction. Flash chromatography (EtOAc/P-ether, 1+1), gave 0.53 g (53% yield) of the title compound as a colourless oil. GC/MS (70 eV) M=319 (3%).

c) (R)-3-(N-Cyclopentyl-N-cyclobutylamino)-8-fluoro-5-hydroxy-3,4-dihydro-2H-1-benzopyran (R)-3-(N-Cyclopentyl-N-cyclobutylamino)-8-fluoro-5-methoxy-3,4-dihydro-2H-1-benzopyran (0.53 g, 1.6 mmol) was dissolved in 47% HBr (15 mL) and stirred at 120° C. for 1.5 h. The solution was cooled by adding ice and alkalised by 14M ammonia. Extractive work-up gave 0.5 g of the title compound as a slightly brown oil. IR contained a typical OH-band at 3654 cm$^{-1}$.

d) (R)-3-(N-Cyclopentyl-N-cyclobutylamino)-8-fluoro-5-trifluoromethylsulfonyloxy-3,4-dihydro-2H-1-benzopyran (R)-3-(N-Cyclopentyl-N-cyclobutylamino)-8-fluoro-5-hydroxy-3,4-dihydro-2H-1-benzopyran was dissolved in a mixture of diethyl ether and methylene chloride (90+10, 20 mL) and triethylamine (0.7 g, 7 mmol) was added and the mixture was cooled to −20 ° C. Trifluoromethanesulfonic anhydride (0.85 g, 3 mmol), dissolved in diethyl ether (10 mL), was added dropwise (5 min). After stirring for 30 min, the dark-brownish mixture was poured into water. The solvent was evaporated. The residue was dissolved in hexane and treated with active charcoal. Filtration trough celite and evaporation of the solvent afforded 0.67 g of the title compound as a colorless oil. GC/MS (70 eV) M=437 (1%).

e) Methyl (R)-3-(N-Cyclopentyl-N-cyclobutylamino)-8-fluoro-3,4-dihydro-2H-1-benzopyran-5-carboxylate (R)-3-(N-Cyclopentyl-N-cyclobutylamino)-8-fluoro-5-trifluoromethylsulfonyloxy-3,4-dihydro-2H-1-benzopyran (0.67 g, 1.5 mmol) (4), DMF (20 mL), triethylamine (0.6 g, 6 mmol), methanol (0.8 g, 12.7 mmol), palladium(II)acetate (22 mg, 0.1 mmol) and 1,3-bis(diphenylphosphino)propane (44 mg, 0.1 mmol) were placed in a round-bottomed flask. The solution was stirred at 75° C. in an atmosphere of carbon monoxide for 4 h. The solvent was removed in vacuo, the residue was dissolved in diethyl ether and treated with active charcoal. Evaporation of the solvent afforded 380 mg of the title compound as an uncolored oil. GC/MS (70 eV) M=347 (3 %).

f) (R)-5-Carbamoyl-3-(N-cyclopentyl-N-cyclobutylamino)-8-fluoro-3,4-dihydro-2H-1-benzopyran Methyl (R)-3-(N-cyclopentyl-N-cyclobutylamino)-8-fluoro-3,4-dihydro-2H-1-benzopyran-5-carboxylate (1.4 g, 4 mmol) was hydrolysed (6M HCl, refluxed for 2 h) and the solvent was removed in vacuo. After drying in air at room temperature over night the crude amino acid hydrochloride was treated with $SOCl_2$ (room temperature for 5 min) to form the acid chloride which after removal of excess $SOCl_2$ in vacuo was dissolved in $CH_2Cl_2$ and added to conc. ammonia to form the amide. The crude product was isolated and purified by flash chromatography to give 220 mg of an uncolored oil which crystallized upon standing. Recrystallization from a mixture of diethyl eter and hexane gave white crystals of the title compound. Yield: 110 mg. Mp: 138°–140° C. $[\alpha]^{20}_D = -146°$ (C=0.2 $CH_2Cl_2$)

PHARMACOLOGY

Pharmacological Treatment of Depression in Man

Evidence is available that in depressed patients the neurotransmission in the central nervous system (CNS) may be disturbed. These disturbances appear to involve the neurotransmitters noradrenaline (NA) and 5-hydroxytryptamine (5-HT). The drugs most frequently used in the treatment of depression are considered to act by improving the neurotransmission of either or both of these physiological agonists. Available data suggest that the enhancement of 5-HT neurotransmission will primarily improve the depressed mood and anxiety, whereas the enhancement of noradrenaline neurotransmission will rather improve the retardation symptoms occurring in depressed patients. In recent years many efforts have been made to develop new drugs with high selectivity for improvement of 5-HT neurotransmission in the CNS.

The dominating mechanism of action for the drugs generally used today in the therapy of mental depression is by blocking the reuptake of the endogenous neurotransmitters (NA and/or 5-HT) released from nerve terminals in the CNS, thus increasing the concentration of these transmitters in the synaptic cleft and hence restoring an adequate neurotransmission.

A fundamentally different way to improve the neurotransmission in the central 5-HT-neurons would be to use a direct 5-HT-receptor antagonist. In order to minimize side effects, a high selectivity for this kind of receptors would then be preferable.

The receptor activity profile, even within a specific sub-receptor group such as $5\text{-HT}_{1A}$ is unpredictable and may result in different pharmacological profiles. For example, two compounds which seem to be closely related in chemical structure may act as agonists on the $5\text{-HT}_{1A}$ autoreceptor while one of these compounds may act as an agonist and the other acts as antagonist on the $5\text{-HT}_{1A}$ postsynaptic receptor. A compound which acts as an antagonist at both pre- and postsynaptic $5\text{-HT}_{1A}$ receptors is by definition an antagonist. Each of these compounds would have a different pharmacological profile and be useful in the treatment of different medical conditions. The differences in receptor activity profiles and resulting pharmacological profiles is set out for the tested compounds in the analysis of the data below.

(i) $5\text{-HT}_{1A}$ receptor binding assay

In order to evaluate the affinity for the $5\text{-HT}_{1A}$-receptor the assay described below using rat brain were used and the $K_i$-value were measured as shown in table 1.

Tissue Preparation: Cerebral cortex and hippocampus from Sprague-Dawley rats were dissected and homogenized in 15 ml ice-cold 50 mM Tris-HCl buffer, pH 7.5, containing 4.0 mM $CaCl_2$ and 5.7 mM ascorbic acid ("Buffer A") with an Ultra-Turrax (Janke & Kunkel, Staufen, FRG) for ten sec. After centrifugation for 12.5 min at 17,000 rpm (39,800×g in a Beckman centrifuge with a chilled JA-17 rotor (Beckman, Palo Alto, Calif., USA)), the pellets were resuspended in buffer A and homogenization and centrifugation repeated. Each pellet was suspended in 5 ml ice-cold 0.32M sucrose and homogenized for 5 sec. The homogenized samples were kept frozen at −70° C. When used, they were diluted with buffer A to 8 mg tissue/ml and homogenized for 10 sec. The tissue homogenates were incubated for then min at 37° C. and then supplied with 10 μn pargyline followed by reincubation for 10 min.

The binding assay followed that described by Peroutka, J. Neurochem. 47, 529–540, (1986), a copy of which is attached as Exhibit 2. Essentially this assay measures the ability of a given competitor molecule to inhibit the binding of $^3$H-8-OH-DPAT to $5\text{-HT}_{1A}$ receptors. The incubation mixture (2 ml) contained $^3$H-8-OH-DPAT (0.25 to 8 nM), the desired concentration of test (competitor) compound and 5 mg/ml tissue homogenate in 50 mM Tris-CHl buffer, pH 7.5, containing 4.0 mM $CaCl_2$ and 5.7 mM ascorbic acid. Six different concentrations of $^3$H-8-OH-DPAT were analyzed. Binding experiments were started by the addition of tissue homogenate and followed by incubation at 37° C. for then min. The incubation mixtures were filtered through Whatman GF/B glass filters with a Brandel Cell Harvester (Gaithersburg, Md., USA). The filters were washed twice with 5 ml ice-cold 50 mM Tris-HCl buffer, pH 7.5, and counted with 5 ml Ultima Gold™ (Packard) in a Beckman LS 3801 scintillation counter. Nonspecific binding was measured by the addition of 10 μM 5-HT to the reaction mixture. The binding data was processed by non-linear least squares computer analysis (Munson and Rodbard, Anal. Biochem. 107, 220–239, (1980)).

Data are presented as $K_i$ values (nM) which are calculated from the $IC_{50}$ value with corrections made for the concentration of the ligand and its affinity constant $K_D$. The $IC_{50}$ value is the concentration of competitor/inhibitor molecule which is sufficient to bind and effectively block one-half the receptor molecules. Each $K_i$ value for a given test compound was obtained by performing the binding assay in duplicate at 10 different concentrations.

TABLE 1

| Examples | $K_i$-value (nM) |
|---|---|
| 1 | 1.76 |
| 2 | 5.45 |
| 3 | 1.07 |
| 4 | <0.3 |
| 5 | 1.17 |
| 6 | 1.75 |
| 7 | 1.5 |
| 8 | 2.53 |
| 9 | 1.52 |

Table 1 shows that the claimed exemplified compounds have high binding affinity to the 5-$HT_{1A}$-receptors.

(ii) Blockade of 5-HT synthesis

The rate of synthesis of 5-hydroxytryptamine (5-HT: serotonin) and dopamine/noradrenaline (DA/NA) is measured as the accumulation of 5-hydroxytryptophan (5-HTP) and (DOPA) 3,4-dihydroxyphenylalanine, (5-HTP) respectively during 30 min after inhibition of aromatic L-amino acid decarboxylase by m-hydroxbenzylhydrazine 2HCl(100 mg/kg i.p.); purchased from Sigma. The test substance is administrated 30 min before m-hydroxbenzylhydrazine 2HCl. The regions of the brain to be examined are rapidly dissected, frozen on dry ice and stored at −70° C. until assayed.

DOPA, 5-HTP and their metabolites are extracted from brain tissue with perchloric acid, containing an internal standard (Isoprenalin), The supernatant from brain homogenate is injected into a liquid chromatographic system comprising a precolumn and an analytical cole. The catechol- and indolamines are detected by coulometric oxidation.

Antagonist at presynaptic 5-$HT_{1A}$ receptors

Minimal effective dose (MED) for blockade of 8-OH-DPAT induced decrease in 5-HT synthesis rate (administrated to rats subcutaneously (SC)/orally (PO).

TABLE 2

| Examples | SC/PO (mg/kg) |
|---|---|
| 1 | 3/- |
| 2 | 3/- |
| 3 | 1/3 |
| 4 | 1/10 |
| 5 | 1/01 |
| 6 | 1/10 |
| 7 | 3/- |
| 8 | — |
| 9 | 1/10 |

Table 2 shows the minimal effective dose after subcutaneous administration for obtaining a significant effect in relation to the minimal effective dose as required to obtain a significant effect after oral administration. The ratio indicates that the claimed exemplified compounds are effective antagonists at the presynaptic 5-$HT_{1A}$ -receptors also after oral administration.

(iii) Block 8-OH-DPAT induced temperature (antagonist)

In each test, thirty rats, weighing approx 250 g, housed in 6 cages of 5 rats, are used. The rats have free access to food and water. Before the start of testing, they are numbered and left undisturbed for at least 1 hour. Before the administration of the compound, the body temperature of each rat is measured using a YSI 2100 tele-thermometer. The thermometer probe is inserted 10 cm into the rectum and left in pace for thirty seconds. The drug is then administered either subcutaneously or orally. In each experiment vehicle and 4 doses of drug are tested. One rat in each cage receives each treatment. The order of treatment is rotated since disturbance to the cage increases the activity of the rats, and thereby their body temperature. Thirth minutes after drug administration the rats' body temperature are measured again. The procedure is repeated 60, 90 and 120 minutes after drug administration. The resultant data on body temperature is subjected to analysis of variance. A significant group by time interaction is taken as an indication of drug effect. To obtain the minimum effective dose, the mean temperature for each of the drug treated groups are compared with that of the vehicle group at each time point, using Dunnett's t-test with a level of significance of $p<0.02$. An indication of bioavailability may be obtained by calculating the ratio between the minimum effective doses following oral and subcutaneous administration.

Antagonist at postsynaptic 5-$HT_{1A}$ receptors Minimal effective dose (MED) for blockade of 8-OH-DPAT induced temperature decrease (administered to rats subcutaneously (SC))/orally (PO).

TABLE 3

| Examples | SC/PO (mg/kg) |
|---|---|
| 1 | 1/3 |
| 2 | 1/10 |
| 3 | 0,01/1 |
| 4 | 0,03/1 |
| 5 | — |
| 6 | 0,03/3 |
| 7 | 0,1/1 |
| 8 | — |
| 9 | — |

Table 3 shows the minimal effective dose after subcutaneous administration for obtaining a significant effect in relation to the minimal effective dose as required to obtain a significant effect after oral administration. The ratio indicates that the claimed examplified compounds is effective antagonists at the postsynaptic 5-$HT_{1A}$ -receptors also after oral administration.

The conclusion from the data in the tables above shows that the claimed compounds are 5-$HT_{1A}$ -receptor antagonists, since they show affinity to the 5-$HT_{1A}$ receptors and act as antagonists on both the presynaptic and the postsynaptic 5-$HT_{1A}$ receptors. Furthermore, the desired effect obtained after subcutaneous as well as after oral administration, strongly supporting a good bioavailability.

We claim:

1. The compound (R)-3-(N-tert-butyl-N-n-propylamino)-5-carbamoyl-8-fluoro-3,4-dihydro-2H-1-benzopyran in the form of the free base or a pharmaceutically acceptable salt thereof.

2. The compound according to claim 1 in the form of the free base.

3. The compound (R)-5-carbamoyl-3-(N,N-dicyclobutylamino)-8-fluoro-3,4-dihydro-2H-1-benzopyran in the form of the free base or a pharmaceutically acceptable salt thereof.

4. The compound according to claim 3 in the form of the free base.

5. The compound (R)-5-carbamoyl-3-(N-cyclobutyl-N-n-propylamino)-8-fluoro-3,4-dihydro-2H-1benzopyran in the form of the free base or a pharmaceutically acceptable salt thereof.

6. The compound according to claim 5 in the form of the free base.

7. The compound (R)-5-carbamoyl-3-(N-cyclobutyl-N-isopropylamino)-8-fluoro-3,4-dihydro-2H-1benzopyran in the form of the free base or pharmaceutically acceptable salt thereof.

8. The compound according to claim 7 in the form of the free base.

9. The compound (R)-5-carbamoyl-3-(N-cyclopentyl-N-cyclobutylamino)-8-fluoro-3,4-dihydro-2H-1-benzopyran in the form of the free base or a pharmaceutically acceptable salt thereof.

10. The compound according to claim 9 in the form of the free base.

11. A pharmaceutical composition containing as active ingredient the compound of any one of claims 1, 8, 9 and 10 in association with a diluent, excipient or inert carrier.

12. A method for treatment of 5-hydroxytryptamine-mediated disorders in the central nervous system of a mammal, which comprises administering to the mammal an effective amount of a compound defined in any one of claims 1–9 and 10.

13. A method according to claim 12 for treatment of depression, anxiety, anorexia, bulimia, senile dementia, migraine, obsessive-compulsive disorder, stroke, Alzheimer's disease, hypertension, gastrointestinal disorders, thermoregulatory and sexual disturbances, pain or disturbances in the cardiovascular system.

14. A process for the preparation of a compound as defined in claim formula I

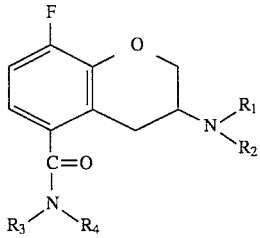

in the form of the free base or a pharmaceutically acceptable salt thereof, wherein $R_1$ is n-propyl or cyclobutyl;

$R_2$ is isopropyl, tertiary butyl, cyclobutyl, cyclopentyl or cyclohexyl;

$R_3$ is hydrogen; and $R_4$ is hydrogen or methyl, which comprises
  i) converting directly the compound of formula IV

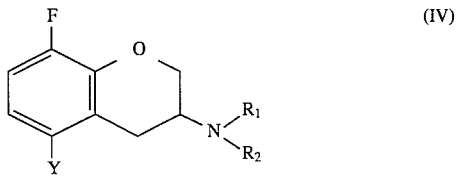

wherein $R_1$ and $R_2$ are as defined above and Y is a leaving group such as $OSO_2CF_3$ or a halide by a catalytic cycle using a zerovalent transition metal such as Pd or Ni and treatment with carbon monoxide followed by amination, or
  ii) converting the compound of formula IV to a compound V

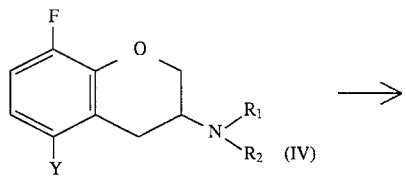

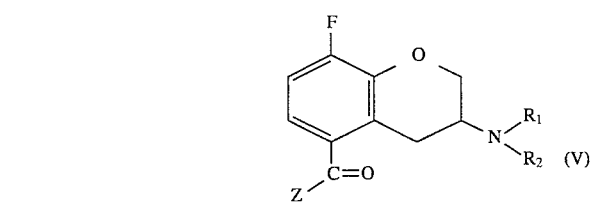

wherein $R_1$ and $R_2$ are as defined above and Z is Cl, Br, OH or $OR_P$, where $R_P$ is $C_1$–$C_6$ alkyl, by a catalytic cycle using a zerovalent transition metal such as Pd or Ni and treatment with carbon monoxide followed by amination of the compound of formula V,
  to give the compound of formula I in its free-base form, which if desired may be converted to a pharmaceutically acceptable salt.

15. A process according to claim 14 wherein the amination is achieved by using ammonia or methylamine.

16. A compound according to claim 1, 3, 5, 7 or 9 in the form of a pharmaceutically acceptable salt selected from the group consisting of hydrochloride, hydrobromide, lactate, acetate, phosphate, sulfate, sulfamate, citrate, tartrate and oxalate.

* * * * *